US007563591B2

(12) United States Patent
Chamoles

(10) Patent No.: US 7,563,591 B2
(45) Date of Patent: Jul. 21, 2009

(54) METHOD FOR ASSAYING THE ACTIVITY OF LYSOSOMAL ENZYMES

(75) Inventor: Nestor A. Chamoles, Buenos Aires (AR)

(73) Assignee: Genzyme Corporation, Cambridge, MA (US)

( * ) Notice: Subject to any disclaimer, the term of this patent is extended or adjusted under 35 U.S.C. 154(b) by 301 days.

(21) Appl. No.: 10/368,589

(22) Filed: Feb. 20, 2003

(65) Prior Publication Data
US 2004/0166554 A1 Aug. 26, 2004

Related U.S. Application Data

(63) Continuation of application No. PCT/US01/26259, filed on Aug. 24, 2001.

(60) Provisional application No. 60/227,573, filed on Aug. 25, 2000.

(51) Int. Cl.
C12Q 1/34 (2006.01)
G01N 33/48 (2006.01)
(52) U.S. Cl. ........................ 435/18; 435/40.5
(58) Field of Classification Search ............ None
See application file for complete search history.

(56) References Cited

U.S. PATENT DOCUMENTS

| | | | |
|---|---|---|---|
| 5,089,392 A | | 2/1992 | Miller et al. |
| 5,281,522 A | * | 1/1994 | Senyei et al. ............ 435/7.9 |
| 5,478,754 A | | 12/1995 | Brandt |
| 5,501,957 A | | 3/1996 | Dennis et al. |
| 5,538,857 A | | 7/1996 | Rosenthal |
| 5,830,912 A | | 11/1998 | Gee et al. |

OTHER PUBLICATIONS

Chamoles et al. Fabry Disease: Enzymatic Diagnosis in Dried Blood Spots on Filter Paper; Clinica Chimica Acta, vol. 308 (2001) pp. 195-196.*
Chamoles et al. Diagnosis of Alpha-L-Iduronidase Deficiency in Dried Blood Spots on Filter Peper: The Possibility of Newborn Diagnosis; Clinical Chemistry, vol. 47, No. 4 (2001) pp. 780-781.*
Hayasaka et al. Regional Distribution of Lysosomal Enzymes in the Retina and Choroid of Human Eyes; Albrecht von Graefes Arch. Klin. Opthamol. vol. 216 (1981) pp. 269-273.*
Zschoche et al Hydrolysis of Lactosylceramide by Human Galactosylceramidase . . . ; Eur. J. Biochem. vol. 222 (1994) pp. 83-90.*
Brenda enzyme database "lysosmal" http://www.brenda.uni-koeln.de, accessed on Internet Dec. 29, 2006.*
Libert et al. Fucosidosis: Ultrastructural Study of Conjunctiva and Skin and Enzyme Analysis of Tears; Investigative Opthamology, vol. 15, No. 8 (1976) pp. 626-639.*
Tsutsumi et al. Application of a Galactosylceramidase Microassay Method to Early Prenatal Diagnosis of Krabbe's Disease; Clinica Chimica Acta, vol. 125 (1982) pp. 265-273.*
Clements et al. Human Alpha-L-Iduronidase; European Journal of Biochemistry, vol. 152, No. 11 (1985) pp. 29-34.*

Database CAPLUS on STN, AN 1998:636798, Guo et al. The Stability of Freeze-Drying Lysosomal Enzymes. Zhonghua Yixue Yichuanxue Zazhi, 1998, vol. 15 No. 3, pp. 167-169.
Database CAPLUS on STN, AN 1993:616954, Schmid et al. Nephrotoxicity of Cyclosporin A in the Rat. II. Reversible Changes in Intranephronal and Urinary Catalytic Activities of N-Acetyl-β-D-Glycosaminidase. Renal Physiol. Biochem. 1993, vol. 16 No. 4, 222-32.
Database CAPLUS on STN, AN 1992:611104, Toldra et al. Enzyme Activities in the Processing of Dry-cured Ham. Proc.—Int. Congr. Meat Sci. Technol., 37th. 1991, vol. 2, pp. 954-957, Publisher: Fed. Cent. Meat Res., Kulmbach, Germany.
Database CAPLUS on STN, AN 1992:445147, Gossrau. R. Histochemical and Biochemical Studies of Dipeptidyl Peptidase I (DPP I) in Laboratory Rodents. Acta Histochem. 1991, vol. 91 No. 1, pp. 85-100.
Lund-Hansen et al. A Quantitative Cytochemical Assay of β-galactosidase in Single Cultured Human Skin Fibroblasts. Histochemistry. 1984, vol. 81 No. 4, pp. 321-330, see entire document.
Database CAPLUS on STN, AN 1978:166436, Rapoport et al. Activation of Intracellular Acid Phosphatase by Dehydration of the Yeast Saccharomyces cerevisiae. Mikrobiologiya, 1978, vol. 47 No. 1, pp. 170-172, (english abstract).
Database CAPLUS on STN, AN 1977:532453, Nestorov et al. The Effect of Freezing and Freeze-Drying on the Activity of Some Lysosomic Enzymes, Fleischwirtschaft. 1977, vol. 57 No. 7, 1335-1336, (english abstract).
Database CAPLUS on STN, AN 1975:14591, Boer et al. Quantitative Lysosomal Enzyme Activity Changes in the Neural Lobe of the Rat Following Water Deprivation and Lactation. J. Neurochem. 1974, vol. 22 No. 6, pp. 965-970.
Database CAPLUS on STN, AN 1974:92464, Giljaard et al. Method for Rapid Prenatal Diagnosis of Glycogenosis II (Pompe's Disease). Clin. Chim. Acta. 1973, vol. 49 No. 2, pp. 361-375.

(Continued)

Primary Examiner—Jon P Weber
Assistant Examiner—Paul C. Martin
(74) Attorney, Agent, or Firm—Bacon & Thomas, PLLC

(57) ABSTRACT

A method, and associated kit, for assaying the activity of lysosomal enzymes present in dried bodily fluids and cell tissue samples, such as α-L-iduronidase, β-D-galactosidase, β-D-glucosidase, chitotriosidase, total α-D-galactosidase and α-D-galactosidase A, hexosaminidase A and B, α-D-mannosidase, β-D-mannosidase, α-L-fucosidase, N-acetyl-α-galactosaminidase, arylsulfatases, sphingomyelinase, β-galactocerebrosidase, iduronate-2-sulfatase and β-D-glucuronidase. The method includes: (a) combining with a dried bodily fluid or cell tissue sample containing at least one type of lysosomal enzyme: (1) an eluent, (2) an incubation buffer and (3) a substrate or substrates capable of reacting with the assayed lysosomal enzymes and producing their corresponding enzyme product or products, (b) allowing the dried bodily fluid or cell tissue sample to react with the eluent, incubation buffer and substrate or substrates for an adequate time and temperature, and (c) applying measuring means to the enzyme product to determine the activities of the lysosomal enzymes present.

34 Claims, 10 Drawing Sheets

OTHER PUBLICATIONS

Database BIOSIS on STN, AN 1992:409205, Van Noorden et al. Assessment of Lysosomal Function by Quantitative Histochemical and Cytochemical Methods. Histochem J. 1991, vol. 23 No. 10, pp. 429-435.

Database MEDLINE on STN, AN 81003131, Galjaard H. Quantitative Cytochemical Analysis of (Single) Cultured Cells. Ciba Foundation Symposium. 1979, vol. 73, pp. 161-180.

Database EMBASE on STN, AN 75120820, Galjaard et al. The Use of Quanitative Cytochemical Analyses in Rapid Prenatal Detection and Somatic Cell Genetic Studies of Metabolic Diseases. Histochemical Journal. 1974, vol. 6 No. 5, pp. 491-509.

Couture et al., A Fluorometric Procedure for Determination of β-Glucosidase. Phytochemistry. 1972, vol. 11, pp. 1947-1949, see entire document.

Database CAPLUS on STN, AN 1980:53905, Kleijer et al. Enzyme Studies on Small Numbers of Cultured Cells. Prenatal. Diagn., Proc. Eur. Conf. Prenatal Diagn. Genet. Disord., $3^{rd}$, 1979, Meeting Date 1978, 298-301. Editors: Murken et al. Publisher: Enke, Stuttgart, Fed. Rep. Ger.

Database CAPLUS on STN, AN 1978:186707, Van Der Veer et al. Lysosomal Enzyme Activities in Different Types of Amniotic Fluid Cells Measured by Microchemical Methods, Combined with Interference Microscopy Hum. Genet. 1978, vol. 40 No. 3, pp. 285-292.

Zhonghua et al., The stability of freeze-drying lysosomal enzymes, PubMed (PMID: 9621127), Jun. 10, 1998;15(3):167-9, abstract only.

\* cited by examiner

METHOD FOR ASSAYING THE ACTIVITY OF LYSOSOMAL ENZYMES

CROSS-REFERENCE TO RELATED APPLICATIONS

This application is a continuation, under 35 USC 120 and 35 USC 365(c), of International Application PCT/US01/26259, filed Aug. 24, 2001 and claims, under 35 USC 119(e) and 35 USC 365, the benefit of U.S. Provisional Application No. 60/227,573, filed Aug. 25, 2000. The teachings of U.S. Provisional Application No. 60/227,573 and PCT/US01/26259 are incorporated herein by reference in their entirety.

TECHNICAL FIELD OF THE INVENTION

This invention relates to a method of assaying lysosomal enzymes present in dried samples of bodily fluids and cell tissues. The invention also relates to a diagnostic kit for assaying lysosomal enzymes present in dried samples of bodily fluids and cell tissues.

BACKGROUND OF THE INVENTION

The lysosome is an organelle founded in the cytoplasm of eukaryotic cells, which serves as storage for many hydrolytic enzymes and as a center for degrading and recycling cellular components. This organelle contains several types of hydrolytic enzymes, including proteases, nucleases, glycosidases, lipases, phospholipases, phosphatases and sulfatases. All enzymes are acid hydrolases. See Lehninger et als, *Principles of Biochemistry*, 2nd ed., Worth Publishers, Inc., New York (1992).

Lysosomal storage diseases ("LSDs") are caused by genetic defects that affect one or more lysosomal enzymes. These genetic diseases result generally from a deficiency in a particular enzyme activity present in the lysosome. To a lesser extent, these diseases may be due to deficiencies in proteins involved in lysosomal biogenesis. At the present, more than 40 distinct LSDs have been identified. Table A relates LSDs to the deficiency of their corresponding factor(s):

TABLE A

| Lysosomal disease | Lysosomal enzyme involved |
|---|---|
| 1. Diseases related to lysosomal enzyme deficiency | |
| Hurler/Scheie syndrome or MPS type I | α-L-iduronidase |
| GM1 gangliosidosis, galactosialidosis and Morquio syndrome B or MPS type IVB | β-D-galactosidase |
| Gaucher disease | β-glucosidase (beta-glucocerebrosidase) |
| Sandhoff disease | β-hexosaminidase β subunit |
| Tay-Sachs disease | β-hexosaminidase α subunit |
| β-mannosidosis | β-D-mannosidase |
| α-L-fucosidosis | α-L-fucosidase |
| Maroteaux-Lamy syndrome or MPS type VI | Arylsulphatase B |
| Metacromatic leukodystrophy | Arylsulphatase A |
| Schindler disease | α-N-acetylgalactosaminidase |
| Aspartylglycosaminuria | Aspartylglucosaminidase |
| Hunter syndrome or MPS type II | Iduronate-2-sulfatase |
| Sanfilippo syndrome A or MPS type IIIA | Glucosamine-N-sulfatase |
| Sanfilippo syndrome B or MPS type IIIB | α-N-acetylglucosaminidase |
| Sanfilippo syndrome C or MPS type IIIC | AcetylcoenzymeA:α-glucosaminide-N-acetyltransferase |
| Sanfilippo syndrome D or MPS type IIID | N-acetylglucosamine-6-sulfatase |
| Morquio syndrome A or MPS type IVA | N-acetylgalactosamine-6-sulfatase |
| Sly syndrome or MPS type VII | β-D-glucuronidase |
| Hyaluronidase deficiency or MPS type IX | Hyaluronidase |
| Multiple sulfatase deficiency | Arylsulphatase A, B, C |
| α-mannosidosis | α-L-mannosidase |
| Sialidosis | α-neuraminidase |
| X-linked ictiosis and multiple sulfatase deficiency | Steroid sulfatase |
| Mucolipidosis II and III | Phosphotransferase |
| Wolman disease | Acid lipase, Tryoleil lipase, Cholesteryl esterase |
| Farber disease | Acid ceramidase |
| Niemann-Pick disease type A and B | Sphingomyelinase |
| Pompe disease or glycogenosis type II | α-glucosidase |
| Neuronal ceroid lipofucsinosis, infantile type | Palmitoyl protein thioesterase |
| Neuronal ceroid lipofucsinosis, late infantile type | Carboxipeptidase |
| Neuronal ceroid lipofucsinosis, juvenile type | Lysosomal membrane protein |
| Krabbe disease | β-galactocerebrosidase |
| Lysosomal acid phosphatase deficiency | Acid phosphatase |
| Pycnodysostosis | Cathepsine K |
| Lysosomal Disease | Transporter protein involved |
| 2. Diseases related to lysosomal transporter protein deficiency | |
| Cystinosis | Cystine transporter |
| Sialic acid storage disease | Sialic acid transporter |
| Cobalamin deficiency type F | Cobalamin transporter |
| Niemann-Pick disease type C | NPC1 free-cholesterol transporter protein |
| Lysosomal Disease | Protein involved |
| 3. Diseases related to lysosomal protective protein deficiency | |
| Galactosialidosis | Neuraminidase, β-galactosidase protective protein |
| Lysosomal Disease | Factor involved |
| 4. Diseases related to lysosomal enzyme activator deficiency | |
| Metacromatic leukodystrophy variant | Saposin B |
| Gaucher disease variant | Saposin C |
| Tay-Sachs disease type AB | β-hexosaminidase activator protein |
| Glycogen storage disease | Unknown |

LSDs are individually rare, although as a group these disorders are relatively common in the general population. The combined prevalence of LSDs is approximately 1 per 5,000 live births. See Meikle et al., *JAMA*, 281:249-254 (1999). Some groups within the population, as for example, descendants of Central and Eastern European (Ashkenazi) Jews are afflicted by a particularly high occurrence of LSDs. For instance, the prevalence rates in the Ashkenazi population of the Gaucher and Tay-Sachs diseases are 1 per 600 and 1 per 3,900 births, respectively.

The Hurler/Scheie syndrome or MPS type I is produced by the deficiency of the lysosomal enzyme α-L-iduronidase. The incidence of this disorder is about 1 in 111,000 births. See Meikle et al., supra. The frequencies for the Hurler and Scheie variants of this disorder are 1 in 100,000 and 1 in 600,000 births, respectively. The Hurler/Scheie syndrome produces a progressive degeneration of the brain, corneal opacities, enlargement of liver and spleen, an important bone dysostosis and a peculiar coarsening of facial features of the patient (Gargoyle face).

The cause of GM1 gangliosidosis is the deficiency of the lysosomal enzyme β-D-galactosidase. The occurrence of this disease is about 1 in 422,000 births. See Meikle et al., supra. GM1 gangliosidosis is a cerebral disease of infantile onset combining dysostosis multiplex, hepato-splenomegaly, cherry red macular spots and progressive neurologic deterioration.

The Gaucher disease is provoked by a deficiency of the lysosomal enzyme β-D-glucosidase. The incidence of this LSD is about 1 in 59,000 births for the general population. See Meikle et al., supra. However, the frequency of Gaucher disease type 1 (nonneuronopathic) in the Ashkenazi population is extremely high. About 1 in 600 births in this group show this particular LSD. Gaucher disease produces a severe hepato-splenomegaly, hematological disturbances, progressive involvement of bones and a severe neurological disease in a limited number of patients.

The chitotriosidase is a lysosomal enzyme that shows usually low activity in the serum and leukocytes of healthy people. However, in LSDs patients, especially in those with Gaucher disease, an increased activity of this enzyme is related with the progression of that disorder. See Young, et al., *J. Inherit. Metab. Dis.,* 20(4): 595-602 (1997). Although the non-specificity of this enzyme limits its diagnostic capability, it is nonetheless, a good parameter to measure treatment effectiveness. See Den Tandt et al., *Biochem. Mol. Med.,* 57:71-72 (1996). The biochemical diagnosis of chitotriosidase deficiency has been described and is known in the art.

Fabry disease is produced by the deficiency of the lysosomal enzyme α-D-galactosidase A. The incidence of Fabry disease is 1 in 117,000 births. See Meikle et al., supra. This LSD is characterized by distinctive skin lesions (angiokeratomes), periodic pain in the extremities, cerebrovascular and cardiovascular diseases and renal involvement.

The Sandhoff disease is caused by a deficiency in the activity of the lysosomal enzyme β-hexosaminidase β-subunit, which is a component of both hexosaminidase A and B. Individuals affected by this disorder show a low or non existent activity for both hexosaminidase A and B (total hexosaminidase). The incidence of this LSD is about 1 in 422,000 births. See Meikle et al., supra. This disorder produces a progressive cerebral degeneration starting at 6 months of age, blindness, hyperacusis and cherry red macular spots.

Tay-Sachs disease is produced by the deficiency of the lysosomal enzyme β-hexosaminidase α-subunit, which is a component of hexosaminidase A. Individuals afflicted by this disorder show a low or non existent activity of hexosaminidase A only. In the absence of hexosaminidase A, the GM2 ganglioside lipid accumulates abnormally in nervous cells causing progressive and irreparable damage to the brain. This LSD is a fatal genetic disorder that causes the degeneration of the central nervous tissue. The disorder is characterized by a progressive cerebral and retinal degeneration that starts in infancy, and is characterized with blindness, hyperacusis, cherry red macular spots and macrocephaly. The destructive process begins in the fetus during early pregnancy, although the disease is not clinically apparent until the child is several months old. The life expectancy of a child afflicted with classical Tay-Sachs disease is 5 years. See http://www.ntsad.org/, National Tay-Sachs & Allied Diseases Association (August 2000). The incidence of Tay-Sachs disease in the general population is approximately 1 in 222,000 births. See Meikle et al., supra. Its incidence is particularly high in descendants of Ashkenazi Jews. About 1 out of every 30 American Jews carries the Tay-Sachs gene. See http://www.ntsad.org/, supra.

The incidence of Mucolipidosis type II/III produced by the deficiency of the lysosomal enzyme N-acetylglucosaminyl-phosphotransferase is about 1 in 422,000 births. See Meikle et al., supra. The prevalence of this disorder is 1 in 325,000 and the estimated carrier frequency of 1 in 285. Both disorders are characterized by short stature, coarse features, joint rigidities, a progressive enlargement of liver and spleen, vertebral anomalies, and a variable degree of mental retardation. Mucolipidosis type II express the most severe phenotype. There is not therapy available for these disorders at the present. These LSDs are related to an increased level of some lysosomal enzymes such as total arylsulfatase (A and B). The abnormal lysosomal enzyme level is attributed to a defective post-translational modification as a consequence of phosphotransferase deficiency.

α-D-mannosidosis disease is provoked by the deficiency of the lysosomal enzyme α-D-mannosidase. The incidence of this disease is about 1 in 1,056,000 births. See Meikle et al., supra. α-D-mannosidosis patients develop severe mental and motor retardation, coarse features, hepato-splenomegaly, dysostosis multiplex, cataracts, corneal opacities and early death.

β-D-mannosidosis is provoked by the deficiency of the lysosomal enzyme β-D-mannosidase. The patients afflicted with this LSD show mental retardation, nerve deafness and angiokeratoma.

The α-L-fucosidosis is provoked by the deficiency of the lysosomal enzyme α-L-fucosidase. Patients afflicted with α-L-fucosidosis develop mental retardation, shortness of stature, coarse features, hepato-splenomegaly, dysostosis multiplex, increased sweet chloride and angiokeratomas.

Other LSDs are less known or has a low incidence in the general population. The biochemical diagnosis and characterization of LSDs has been widely reviewed and is known in the art. See Wenger et al., *Techniques in Diagnostic Human Biochemical Genetics, A Laboratory Manual*, pp. 587-617, F. A. Hommes Ed., Wiley-Liss, Inc. New York, N.Y. (1961); *Practical Enzymology of the Sphingolipidoses*, R. H. Glew and S. P. Peters, Eds., pp. 173-216, Alan R. Liss, Inc., NY (1977).

At the present most LSDs, such as α-D-mannosidosis, β-D-mannosidosis, α-L-fucosidosis and the Sandhoff and Tay-Sachs diseases, do not have an indicated therapy. Other LSDs, like for instance, late stage GM1 gangliosidosis, demand risky and costly therapeutical procedures such as bone marrow transplants.

Lately, recombinant proteins have been used for the treatment of some LSDs. Individuals afflicted with the Hurler/Scheie, Gaucher and Fabry diseases have been treated successfully with recombinant α-L-iduronidase, β-glucosidase and α-D-galactosidase, respectively. See Kakkis et al., *Abstracts of the Joint Meeting of International Symposium on Innovative Therapies & 6th International Symposium on Mucopolysaccharidosis & Related Diseases*, p. 23, May 19-21, Minneapolis, Minn., USA (2000); Grabowski et al., *Blood Reviews,* 12:115-133 (1998); Schiffmann, et al., *J. Clin. Invest.,* 97:365-370 (2000). The application of recombinant proteins have shown promising result in the treatment of other LSDs, such as Pompe disease, now in Phase II clinical trials.

The positive effects of the known therapies, particularly for those LSDs involving central nervous system and bone pathologies, rely heavily on the early diagnosis and treatment of the disorder. A timely diagnosis may prevent the occurrence of irreversible damages in the patient. This consideration is especially true for LSDs where bone marrow transplant therapy is indicated. In these cases an early diagnosis of the LSD will allow clinicians to take advantage of the opportunity presented by the naturally suppressed immune system of the neonate thus enhancing the chances of a successful engraftment. See Ida et al., *Abstracts of the Joint Meeting of International Symposium on Innovative Therapies & 6th International Symposium on Mucopolysaccharidosis & Related Diseases*, May 19-21, Minneapolis, Minn., USA (2000).

Symptomatic LSDs patient show a high intralysosome storage of abnormal material. This situation is treated, when possible, by applying frequently high doses of recombinant enzymes to the LSD patient. At the present, this procedure entails administering intravenously the recombinant enzyme to the patient in order to assure that a sufficiently high level of enzyme will available in the body to degrade the abnormal material. If the LSD diagnosis is made in a pre-symptomatic stage, as for example, in newborns, the intralysosome storage of the abnormal material may be prevented. An early detection of these disorders will make possible to treat the LSD patient less frequently and with lower doses of recombinant enzyme. In addition, a reduced dosage treatment will also make possible to utilize less invasive routes of drug delivery like oral and nasal administration.

At the present, LSDs are diagnosed by DNA-based and enzymatic activity assays. Under DNA-based assays, a known mutation of a lysosomal enzyme gene is detected by hybridizing or sequencing part of the relevant enzymatic gene. See U.S. Pat. No. 5,710,028 (to Eyal et al.); U.S. Pat. No. 5,234,811 (to Beutler et al.); U.S. Pat. No. 5,217,865 (to Myerowitz). On the other hand, enzymatic activity assays implies measuring the amount of substrate or enzyme product related to a particular lysosomal enzyme by utilizing fluorogenic, spectrophotometric and radioactive analysis. See Wenger et al., supra.

For DNA-based assays, a specific region of DNA is amplified by a polymerase chain reaction. The amplified region is either sequenced entirely looking for mutations or hybridized with specific probes to detect a specific mutation in a lysosomal enzyme gene. However, the application of these techniques to LSD detection has been restricted by the following limitations:

1) In hybridization assays the test is limited to known mutations of the lysosomal enzyme under study. This method will not detect patients showing LSD symptoms if the LSD is caused by an unknown genetic mutation of the relevant lysosomal enzyme.

2) For sequencing assays the detection of a new mutation does not imply necessarily that the subject will develop the related LSD. For sequencing assays it is unfeasible to detect carrier individuals. Carrier detection must be done by hybridization assays.

The lysosomal enzyme activity assays known in the art not based in DNA technology have also several restrictions in their application. One of their principal limitations is the minimum sample volume (usually between 5 to 10 ml of blood) necessary for testing. This volume is too high to allow infants to stand neonatal screening for these disorders. The consequences of this limitation are substantial. In most LSDs cases, a second diseased child is born to LSD carrier parents before the first born is identified as a LSD patient. The timely screening of the first born would prevent the development of the disorder and improve the chances of effective treatment for the rest of his siblings.

Another inconvenience of the enzymatic activity assays is that the sources of samples more commonly utilized for these tests (whole blood, plasma and serum) must be stored under controlled conditions and only for limited periods of time (no more than 3 days). These restrictions limit considerably the time that may lapse between the sample collection and the enzymatic activity assay.

Two additional limitations of the known lysosomal enzyme activity assays are their complexity and unavailability. Leukocyte isolation and purification from blood is a very specialized and tedious laboratory procedure. In addition, these assays are not performed in routinary clinical testing. These conditions restrict considerably the access of the general population to this type of tests. See Wenger et al., supra.

Recently, U.S. Pat. No. 5,719,035 (to Rosenthal et al.) have described a method for assaying enzyme activity in blood. This method discloses the determination of erythrocyte enzyme activities such as biotinidase and galactose-1-phosphate uridyl transferase (GALT). This method uses whole liquid blood and refers to the detection of non-lysosomal enzymes. The method revealed by Rosenthal also requires that hemoglobin be precipitated for testing.

A method for the diagnosis of LSDs using fluorophore assisted carbohydrate electrophoresis is also known in the art. See U.S. Pat. No. 5,205,917 (to Klock). However, this method does not provide a conclusive LSD diagnosis. The method is unable to identify the specific deficient lysosomal enzyme. In practice this method is complemented with other conventional enzyme activity assays for LSDs diagnosis because of its unreliability.

Singer et al. have described a method for determining the activity of lysosomal enzymes by using tears collected on filter paper and then storing immediately the collected samples in a buffer. The method was applied to the detection of Tay-Sachs and Fabry diseases in newborns. See Singer et al., *Lancet* 2:1116 (1973). However, this method is not used in routine clinical practice, especially for newborns. The method requires that tears be collected by applying strands of filter paper to the patient eyes. This procedure is extremely uncomfortable to patients, especially infants, and sample collection is difficult. In addition, a relative high volume of tears is required for testing. It is frequently necessary to repeat sampling when using his method because the amount of sample collected is insufficient for assay.

In addition, Hopwood et al. have disclosed a method for measuring a lysosome-associated membrane protein (LAMP-1) as a LSD diagnostic marker. See Hopwood et al., *Clinical Chem.*, 45(8):1325-1335 (1997). The method attempts to determine indirectly the activity of lysosomal enzymes. However, this method fails to distinguish clearly between healthy and diseased individuals and has been found to be irreproducible in practice.

DESCRIPTION OF THE INVENTION

The present invention provides an inexpensive and simple method for the determination of LSDs. The claimed method offers several advantages, including a simple and expedite sample collection, minimal invasiveness, reduced sample volume, easy sample handling and storage for extended periods of time. The claimed method makes economically viable the massive screening of the population for LSDs. In addition, the present invention may be used for assaying the activity of any lysosomal enzyme, in any sample containing lysosomal enzymes.

Another benefit of the present invention is its ability to discriminate clearly between healthy and diseased individuals for all LSDs. The claimed method may also differentiate between carriers and individuals afflicted for some LSDs.

An additional benefit of the claimed invention is its universal application. The method described utilizes small amounts of sampling material allowing the effective prenatal and neonatal LSDs screening of the population. For treatable LSDs, the early detection made possible by the claimed invention allows the timely diagnosis and treatment of newborns thus minimizing any irreparable damages they may suffer as a consequence of these disorders. At a pre-symptomatic stage, the claimed method would make possible to treat LSDs patients with lower doses of recombinant enzymes, thus facilitating the development of less invasive treatments such as nasal and oral drug administration.

Another advantageous aspect of the present invention is the long period of time for which the dried samples could be stored without losing their diagnostic capability. This characteristic of the claimed method makes possible sending samples for screening by regular mail. The LSDs screening of populations located in remote places or without the necessary medical technology for performing this kind of assays, as in developing countries, is thus facilitated.

Another advantageous aspect of the present invention is its capacity to determine reliably the activity of lysosomal enzymes utilizing samples stored for several years and under adverse environmental conditions. The claimed method may distinguish clearly between LSDs patients and healthy individuals utilizing samples taken up to 5 years before performing the enzymatic assay. The claimed method is effective even if the samples are kept at room temperature during the totality of such long periods of time. This aspect of the claimed method enables the retrospective and forensic analyses of patients affected with LSDs.

An additional benefit of the claimed method is the sample physical support does not interfere with the enzymatic activity determination. Contrary to the conventional practice in the art, the claimed method does not require that the sample physical support be removed from sample solution during testing.

The claimed invention is also a more precise and comprehensive test than DNA methods used for LSDs screening. Most of the conventional DNA methods are limited to detect known mutations of lysosomal enzyme genes. This limitation makes it impossible to detect individuals afflicted by other genetic mutations of these enzymes. In addition, the detection of a mutation in the gene of a lysosomal enzyme is not conclusive as to the development of a LSD in the mutation carrier. The claimed method is capable of detecting LSD patients regardless of the mutation causing their particular enzymatic dysfunction.

The claimed method may also be beneficial in the research and development of recombinant enzymes for the treatment of LSDs. The present invention may be used to screen transgenic animals made deficient in a particular lysosomal enzyme, thus enabling the development of animal models to study LSDs. The claimed method may also be used for quality control purposes as an in vitro biological activity assay in the production of recombinant lysosomal enzymes.

Table B discloses the abbreviated substrate names and their related lysosomal enzymes.

TABLE B

| Substrate | Enzyme |
| --- | --- |
| MU-α-L-iduronide | α-L-iduronidase |
| MU-β-D-galactoside | β-D-galactosidase |
| MU-β-glucuronic acid or phenolphthalein-β-D-glucuronic acid | β-D-glucuronidase |
| MU-α-L-fucoside | α-L-fucosidase |
| MU-α-mannoside | α-mannosidase |
| MU-β-D-mannoside | β-D-mannosidase |
| 4-nitrocathecol sulfate or MU-sulfate | Arylsulfatase |
| MU-β-D-N-acetylglucosaminide | β-hexosaminidase |
| MU-β-D-N-acetylglucosaminide-sulfate | β-hexosaminidase A |
| MU-β-D-glucosaminide | β-D-glucosidase |
| MU-α-D-galactoside | α-D-glucosidase |
| MU-α--neuraminic acid | α-neuraminidase |
| MU-α-D-N-acetylgalactosaminide | α-D-N-acetylgalactosaminidase |

The following abbreviations will also be used in this disclosure:

MU—4-methylumbelliferyl
MPS—Mucopolysaccharidosis
MSD—Multiple sulfatase deficiency
TRIS—Tris(hydroxyethyl)aminomethane In its broadest terms, the present invention is a method for assaying the activity of a lysosomal enzyme present in a dried sample of a bodily fluid or cell tissue sample, said method comprising:

(a) combining a dried sample of bodily fluid or cell tissue with
  (1) an eluent,
  (2) an incubation buffer and
  (3) at least one substrate capable of reacting with said lysosomal enzyme and generating at least one enzyme product, to form an incubation media,
(b) incubating said media under conditions sufficient to generate said enzyme product; and
(c) applying measuring means to said enzyme product to determine the activity of said lysosomal enzyme.

The procedures (1) through (3) in step (a) can be performed simultaneously or in any given order. It is preferred that procedures (1) through (3) in step (a) be performed sequentially in the following order: (1), (2) and (3).

The sample according to the present invention may be in the form of a dried bodily fluid or a cell tissue. It is preferred that the sample be in a form of a dried bodily fluid. When a dried bodily fluid sample is utilized, it is preferred a form selected from the group consisting of blood, semen, urine, saliva, amniotic liquid or cerebrospinal liquid. The most preferred form of dried bodily fluid is blood. The dried sample shall be of mammalian origin, preferably of sheep, mouse or human origin. Most preferably, the sample is of human origin.

It is preferred that the sample be placed and dried in a suitable physical support. Preferably, the physical support should have a porous surface. Most preferably, the physical support is filter paper.

The dried samples prepared according to the present invention may be stored for long periods of time under adequate temperature conditions prior to testing. It is preferred that the dried samples be stored for less than 40 days, and more preferably, for less than 20 days. It is most preferred that the dried samples be stored for less than 72 hours before testing. The dried samples prepared according to the present invention may be stored at a temperature of less than 25° C. It is more preferred that the dried samples be stored at less than 4° C.

According to the present invention the eluent must be able to release the assayed lysosomal enzyme from the dried sample to the reaction media Examples of suitable eluents that may be utilized according to the claimed method are D-saccharic acid-1,4-lactone, sodium chloride, sodium taurocholate, sodium acetate, water, N-acetyl-D-galactosamide, citrate-phosphate buffer, lead acetate, sodium taurocholate and Triton X-100.

Generally, lysosomal enzymes are active under acidic conditions. Consequently, the incubation buffer utilized according to the present invention shall have a pH value of less than 7. Preferably, the pH value of the incubation buffer is between 2.5 and 5.5, and most preferably, between 2.8 and 5. Examples of incubating buffers that may be utilized in accordance with the present invention are sodium acetate, sodium citrate, sodium formate, sodium phosphate buffers and mixtures thereof appropriate for performing aqueous assays of biological materials. In several embodiments of the present invention an incubation buffer may also be utilized as eluent.

A substrate according to the present invention is any natural or synthetic molecule capable of producing a measurable signal after being converted by a lysosomal enzyme. Preferably, the substrate is a synthetic molecule comprising a natural substrate of the lysosomal enzyme linked to a fluorophoric, chromophoric or radioactive moiety. A measurable signal is obtained after the moiety is cleaved by a lysosomal enzyme. When a fluorophore is utilized it is preferred a 4-methylumbelliferyl group, while 4-nitrocathecol, phenolphtalein or p-nitrophenyl groups are preferred when a chromophore is used. When a radioactive moiety is utilized, $^{14}C$ sphingomyeline and $^{3}H$ galactosylceramide are preferred.

In an embodiment of the present invention, the combined dried sample, eluent, incubation buffer and substrate(s) ("the incubation media" or "sample incubation") are incubated under conditions sufficient to generate the enzyme product; i.e., for an adequate time and temperature. The adequate incubation time is dependent on the assayed lysosomal enzyme. Each lysosomal enzyme has a characteristic incubation time curve and an optimal incubation time. For optimal results it is preferred that the incubation temperature be the physiological temperature. When a human origin sample is assayed it is preferred that 37° C. be the incubation temperature.

It is preferred that the sample incubation be halted prior to measurement. The sample incubation may be interrupted by any non-interfering means, such as the application of heat, dilution, a change of pH or the addition of any deproteinizing agent as trichloroacetic acid (TCA) or organic solvents.

Preferably, the incubation is halted by changing the pH of the reaction. It is further preferred that a suitable stopping buffer be utilized for this purpose. Preferably, the stopping buffer has a pH value between 7 and 12, and most preferably, between 10 and 11. Preferably, the stopping buffer is a glycine-sodium carbonate or an ethylenediamine buffer.

The disappearance of a measurable substrate or the appearance of a measurable enzyme product may allow the determination of the enzyme activity. In the present invention it is preferred that the activity be measured by the appearance of a measurable enzyme product. The amount of enzyme product is determined by applying measuring means to the reaction media. As measuring means according to the present invention a fluorometer, calorimeter, spectrophotometer or radioactivity analyzer may be utilized. It is preferred that a fluorometer be utilized as measuring means.

As used herein, the term "activity" shall be construed to comprise the formation of an enzyme product or the conversion of a substrate under the action of an enzyme.

As used herein, the term "blood" shall be construed to include any blood-containing fluid or blood product, such as whole blood, plasma, serum, isolated blood cells or a lysate made from whole blood and derivatives thereof.

As used herein, the term "bodily fluid" shall be construed to include a form selected from the group consisting of blood, semen, urine, saliva, amniotic liquid or cerebrospinal liquid, preferably blood, and most preferably whole blood.

As used herein, the term "cell tissue" shall be construed to comprise any eukaryotic cell type, such as chorionic villae, fibroblasts, amniocytes, hepatocytes, epidermal, epithelial and muscle cells taken directly from the body or cultured cells. This term shall also be construed to comprise a lysate of the cells enumerated herein.

As used herein, the term "diluent" shall include any reagent to dissolve either the substrate or the signal standard for calculating the amount of enzyme product. Examples of diluents are distilled water and incubation buffers.

As used herein, the term "dried bodily fluid sample" shall be construed to include any form of bodily fluid dehydrated either naturally by exposing a bodily fluid sample for a time sufficient to substantially remove all fluid therefrom, such as for example 12 hours or more to room temperature (approx. 22° C.). One person skilled in the art will be able to ascertain the proper conditions to dry efficiently and rapidly the sample without denaturing or damaging the enzymes being assayed. This determination could be done without undue experimentation by the assayer.

As used herein, the term "dried cell tissue sample" shall be construed to include any form of cell tissue dehydrated naturally by exposing a cell tissue sample for sample for a time sufficient to substantially remove all fluid therefrom, such as for 6 hours or more to room temperature (approx. 22° C.). One person skilled in the art will be able to ascertain the proper conditions to dry efficiently and rapidly the sample without denaturing or damaging the enzymes being assayed. This determination could be done without undue experimentation by the assayer.

Preferably, a "dried sample" is meant to define a sample that remains dry for more than just a transient amount of time, or one that remains dry at more than only at certain spatial portions thereof.

As used herein, the term "eluent" shall be construed to include any substance capable of releasing a lysosomal enzyme from a dried bodily fluid or dried cell tissue sample to the reaction media. Examples of eluents are water, sodium taurocholate, triton X-100, D-saccharic acid-1,4-lactone and the mixtures thereof.

As used herein, the term "enzyme product" shall include any product of the catalytic action of an enzyme over a substrate. An example of an enzyme product is the fluorescent product generated when a marker molecule is hydrolyzed or otherwise cleaved from an artificial substrate (e.g. 4-methylumbelliferone is formed by the action of β-galactosidase on MU-β-galactoside).

As used herein, the term "high enzyme activity control" shall include any sample or material containing at least one type of active lysosomal enzyme. Examples of high enzyme activity controls are human or animal bodily fluids or tissues and recombinant or extractive lysosomal enzymes.

As used herein, the term "incubation buffer" shall be construed to comprise any solution providing the adequate pH and ionic strength necessary for maintaining or optimizing enzyme activity. Examples of incubation buffers are sodium formate, sodium citrate, sodium phosphate, sodium acetate and the mixtures thereof.

As used herein, the term "low enzyme activity control" shall include any sample or material containing at least one type of inactive or low activity lysosomal enzyme. Examples of low enzyme activity controls are human or animal bodily fluids or tissues and recombinant or extractive lysosomal enzymes. A special example is a dried human blood spotted punch incubated for 5 minutes in boiling water.

As used herein, the term "lysosomal enzyme" shall be construed to comprise enzymes present in the lysosome and other enzymes intervening in lysosomal biogenesis. Table A enumerates most of the lysosomal enzymes known in the art.

As used herein, the term "sample" shall be construed to include any form of bodily fluid or cell tissue containing at least one type of lysosomal enzyme.

As used herein, the term "stopping buffer" shall be construed to comprise any solution providing the adequate pH necessary for halting or minimizing enzyme activity. Examples of stopping buffers are glycine, sodium carbonate, sodium hydroxide, ethylenediamine, TRIS and the mixtures thereof.

As used herein, the term "substrate" shall include any natural or synthetic molecule susceptible of being converted by an enzyme. Table B enumerates most of the substrates of lysosomal enzymes known in the art.

The claimed invention is an improvement over the known conventional methods for several reasons.

The inventive method does not require that the sample be processed before testing. All conventional known methods require that some degree of sample handling (e.g. centrifugation, chemically induced lysis) be performed before testing. Under the conventional methods, the enzymatic activity determinations are performed on derivatives of whole blood (lymphocytes, cultivated fibroblasts, serum) but not directly upon the unprocessed whole blood as in the method of the invention.

The conventional methods require that the assay be performed almost immediately following sample collection. Under the known methods it is impossible to store the sample for long periods of time and then perform the assay. In contrast the dried sample may be stored for long periods of time and assayed much later after collection. Under the inventive method clearly distinguished results can be obtained up to 4 years after sample collection.

The conventional methods require that the sample be assayed within a short period of time after sample collection based upon the premise that the activity of lysosomal enzymes decay with time, and therefore reliable results may not be obtained if some time has passed after sample collection. The inventive method, in contrast, has demonstrated that the activity of lysosomal enzymes is preserved over time.

Moreover, the invention has demonstrated, contrary to prior beliefs, that the longer the period of sample incubation the larger the differences between the lysosomal enzymatic activity of LSDs patients and healthy individuals. This enhanced differentiation impinges directly upon the accuracy of LSD diagnosis if the inventive method is utilized. The method distinguishes in all cases between diseased and healthy individuals. In some cases even LSD carriers may be clearly distinguished with this method.

The inventive method is substantially less expensive than the most utilized conventional method for determining lysosomal enzymes activities.

The invention also relates to a diagnostic kit for determining the activity of lysosomal enzymes using the inventive method described herein. The diagnostic kit comprises a carrier and containers therein. In an embodiment, the diagnostic kit comprises a test tube, a first container containing an eluent, a second container containing an incubation buffer, a third container containing at least one substrate, a fourth container comprising a stopping buffer, a fifth container containing a standard for measuring the amount of enzyme product, a sixth container comprising a diluent, a high enzyme activity control, and a low enzyme activity control. In various embodiments of the invention, the diluent includes distilled water and/or incubation buffers; the high enzyme activity control and the low enzyme control may include animal and/or human samples and/or recombinant and/or extractive lysosomal enzymes; the substrate(s) may be in stabilized form and/or in dry form; the substrate(s) may be coated on the test tube; the test tube may be in a multiwell format; and/or the multiwell format may be coated with the substrate(s). An embodiment of the diagnostic kit of the invention is discussed in more detail in Example 24 and such discussion is incorporated herein.

DETAILED DESCRIPTION OF THE PREFERRED EMBODIMENTS

EXAMPLE 1

Preparation of Dried Blood Samples

Figure 1:
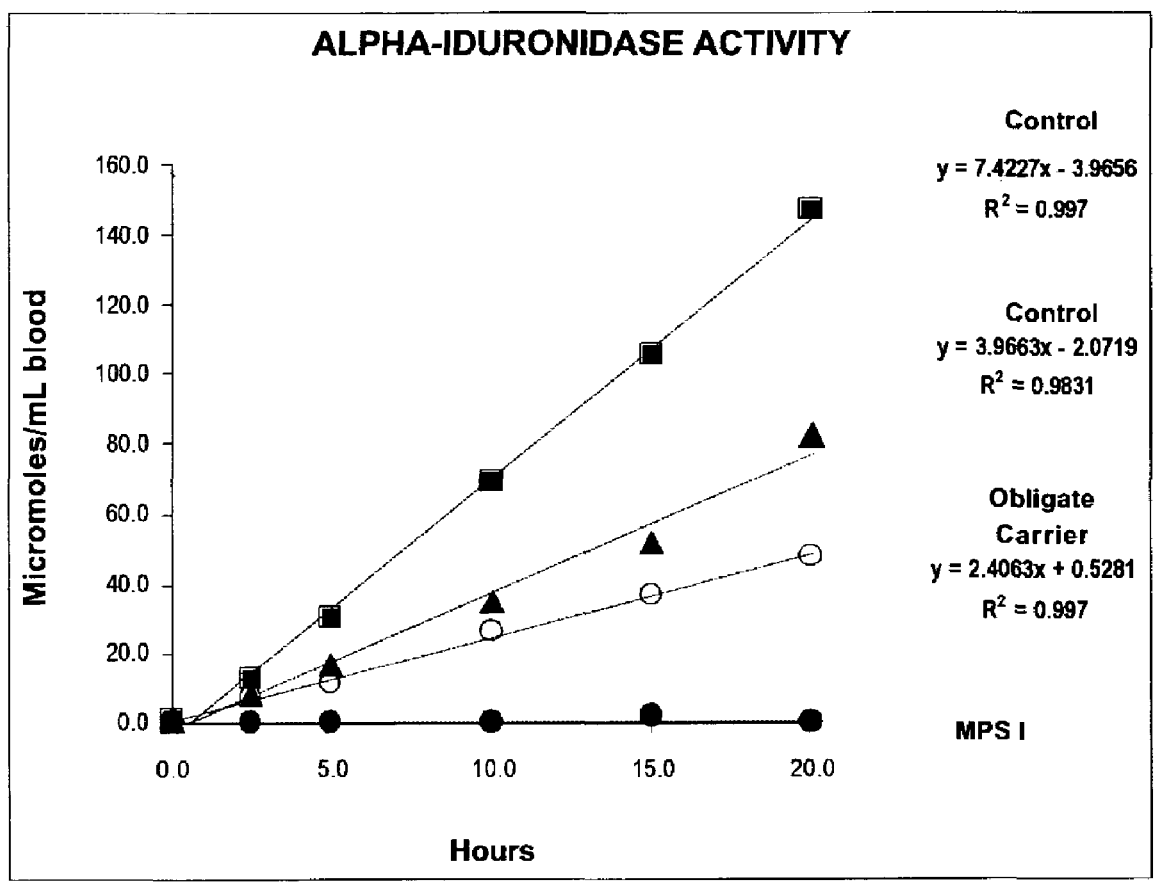
FIG. 1 illustrates the amount of hydrolyzed MU-α-L-iduronide at variable incubation times. Each point represents the average of duplicate determinations.

A drop of blood obtained by venepuncture was spotted on filter paper (Schleicher and Schuell N° 903, Keene, N.H., USA) and allowed to dry at room temperature (22° C.) overnight on a flat non-absorbing surface. The dried blood spots on filter paper were stored on plastic bags at 4° C. until analysis.

A sample for analysis was prepared by punching out a 3 mm-diameter circle (about 5.5 µl of whole blood) with a standard paper punch from the dried blood spots on the filter paper. A sample for analysis was prepared by punching out a 1.5 mm-diameter circle (about 2 µl of whole blood) with a standard paper punch from the dried blood spots on the filter paper.

This protocol was also performed by utilizing a heelprick finger to obtain the blood.

EXAMPLE 2

Preparation of Dried Chorionic Villae Samples

A chorionic villae sample (about 10 mg) was sonicated twice by 20 seconds in 50 µl of cold distilled water (Heat Systems-Ultrasonics, Inc., model W225R).

After removing 10 µl for protein determination, the sonicated cells were spotted on filter paper (Schleicher and Schuell N° 903, Keene, N.H., USA) and allowed to dry for 6 hours at room temperature (22° C.) on a flat non-absorbing surface. See Lowry et al., *J. Biol. (hem.* 193:265-275 (1951). The spotted filter paper was stored on plastic bags at −20° C. until analysis.

A sample for analysis was prepared by punching out a 3mm-diameter circle with a standard paper punch from the dried chorionic villae spots on the filter paper.

EXAMPLE 3

Preparation of Dried Cultured Amniocytes Samples

Cultured amniocytes were suspended in 500 µl of cold phosphate saline buffer (pH 7.4). After centrifugation at 1,200 g for 5 minutes at 4° C. the supernatant was removed by aspiration. The cell pellet was resuspended in 40 µl of cold distilled water and sonicated (Heat Systems-Ultrasonics, Inc., model W225R).

After removing 10 µl for protein determination, the sonicated cells were spotted on filter paper (Schleicher and Schuell N° 903, Keene, N.H., USA) and allowed to dry for 6 hours at room temperature (22° C.) on a flat non-absorbing surface. See Lowry et al., supra. The spotted filter paper was stored on plastic bags at −20° C. until analysis.

A sample for analysis was prepared by punching out a 3 mm-diameter circle with a standard paper punch from the dried amniocytes spots on the filter paper.

EXAMPLE 4

Detection of Hurler/Scheie Syndrome

Determination of α-L-iduronidase Activity in Dried Blood Spots

A) To a 1-ml disposable test tube the following were added sequentially:
1) A 3 mm-diameter punch (5.5 µl of blood) prepared according to the protocol indicated in Example 1,
2) 40 µl of 0.05 M sodium formate buffer (pH 2.8) containing 0.3 µg of D-saccharic acid-1,4-lactone as eluent, and
3) 20 µl of 2 mM MU-α-L-iduronide in distilled water as substrate.

B) The test tube was vigorously mixed by vortex (Vortexer Luckham, model V 400, USA) for 1 minute, placed then in a shaking water bath and incubated for 20 hours at 37° C.

C) After incubation, the test tube was placed in an ice bath and 300 µl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 µl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. The enzyme activity was expressed as micromoles of hydrolyzed substrate per liter of blood per hour.

This assay was also performed with sheep and murine blood using the same protocol described above.

This assay was also performed by utilizing ethylendiamine as stopping buffer.

FIG. 1 illustrates the amount of hydrolyzed MU-α-L-iduronide at variable incubation times. In the Figure, the Controls represented by the square and triangular points refer to healthy adults and healthy newborns, respectively.

Table 1 shows the results obtained for MPS I cases, MPS I obligate carriers, healthy adults and newborns, sheep and mouse.

TABLE 1

| α-L-iduronidase activity (mmol/L blood/h) | |
| --- | --- |
| MPS I (n = 13) Range | 0-0.3 |
| Obligate carriers (n = 10) Range | 1.3-3.8 |
| Healthy adults (n = 50) Range | 1.5-6.7 |
| Healthy newborns (n = 25) Range | 2.6-6.7 |
| Sheep (n = 1) | 2.6 |
| Mouse (n = 3) | 4.2-7.4 |

EXAMPLE 5

Detection of GM1 gangliosidosis

Determination of ∃-D-galactosidase Activity in Dried Blood Spots

A) To a 1-ml disposable test tube the following were added sequentially:
1) A 3 mm-diameter punch (5.5 µl of human blood) prepared according to the protocol indicated in Example 1,
2) 40 µl of 0.05 M citrate-phosphate buffer (pH 4.4) in 0.45% (w/v) sodium chloride as eluent, and
3) 20 µl of 0.8 mM MU-β-D-galactopyranoside in distilled water as substrate.

B) The test tube was vigorously mixed by vortex (Vortexer Luckham, model V 400, USA) for 1 minute, placed then in a shaking water bath and incubated for 3 hours at 37° C.

C) After incubation, the test tube was placed in an ice bath, and 300 µl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 3 hours. The reaction was immediately halted by adding 300 µl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with sheep and murine blood using the same protocol described above.

This assay was also performed by utilizing ethylendiamine as stopping buffer.

Figure 2:
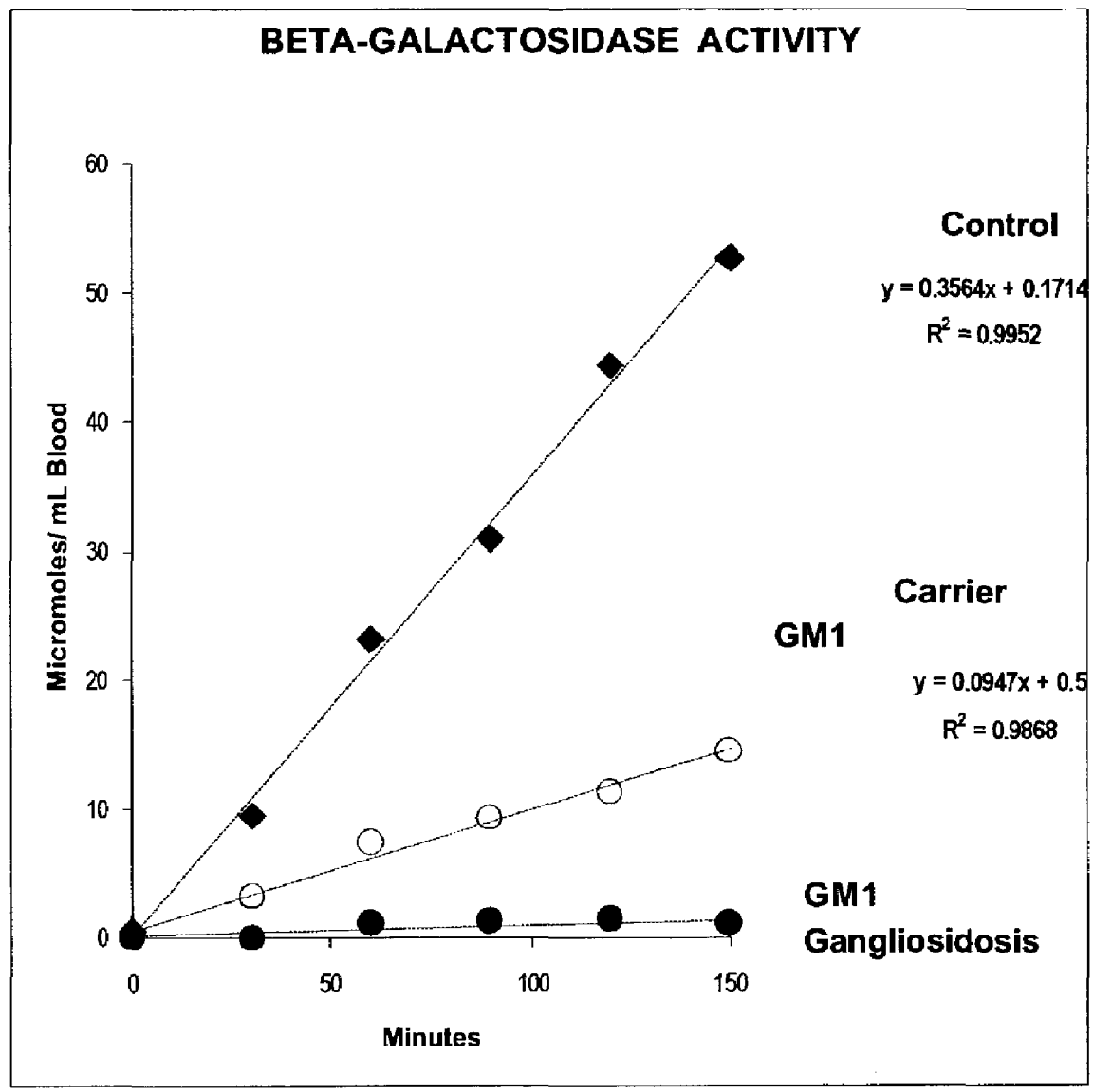
FIG. 2 illustrates the amount of hydrolyzed MU-β-D-galactopyranoside at variable incubation times. Each point represents the average of duplicate determinations.

FIG. 2 illustrates the amount of hydrolyzed MU-β-D-galactopyranoside at variable incubation times. In the Figure, the Control represented by the square points refers to healthy adults.

Table 2 shows the results obtained for GM1 gangliosidosis cases, obligate carriers of GM1 gangliosidosis, galactosialidosis case, obligate carriers of galactosialidosis, healthy adults and newborns, sheep and mouse.

TABLE 2

| β-D-galactosidase activity (mmol/L blood/h) | |
|---|---|
| GM1 Gangliosidosis (n = 10) Range | 0-0.5 |
| GM1 obligate carriers (n = 11) Range | 2.7-6.5 |
| Galactosialidosis (n = 1) | 0.7 |
| Galactosialidosis obligate carrier (n = 1) | 21.8 |
| Healthy adults (n = 50) Range | 10.5-29.0 |
| Healthy newborns (n = 35) Range | 16.5-48.1 |
| Sheep (n = 1) | 8.3 |
| Mouse (n = 2) | 10.5-16.6 |

EXAMPLE 6

Detection of Gaucher Disease

Determination of β-D-glucosidase Activity in Dried Blood Spots

A) To a 1-ml disposable test tube the following were added sequentially:
1) A 3 mm-diameter punch (5.5 µl of human blood) prepared according to the protocol indicated in Example 1,
2) 40 µl of 0.75% (w/v) sodium taurodeoxycholate in distilled water,
3) 30 µl of 0.4 M citrate-phosphate buffer (pH 5.4), as eluent, and
4) 50 µl of 20 mM MU-β-D-glucopyranoside in distilled water as substrate.

B) The test tube was vigorously mixed by vortex (Vortexer Luckham, model V 400, USA) for 1 minute, placed then in a shaking water bath and incubated for 20 hours at 37° C.

C) After incubation, the test tube was placed in an ice bath, and 300 µl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 µl of 0.085 M glycine-sodium carbonate buffer to the blank sample. The fluorescence reading for the assayed sample was determined by subtracting the value of the blank sample to the enzyme product. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with sheep and murine blood using the same protocol described above.

This assay was also performed by utilizing ethylendiamine as stopping buffer.

Figure 3:
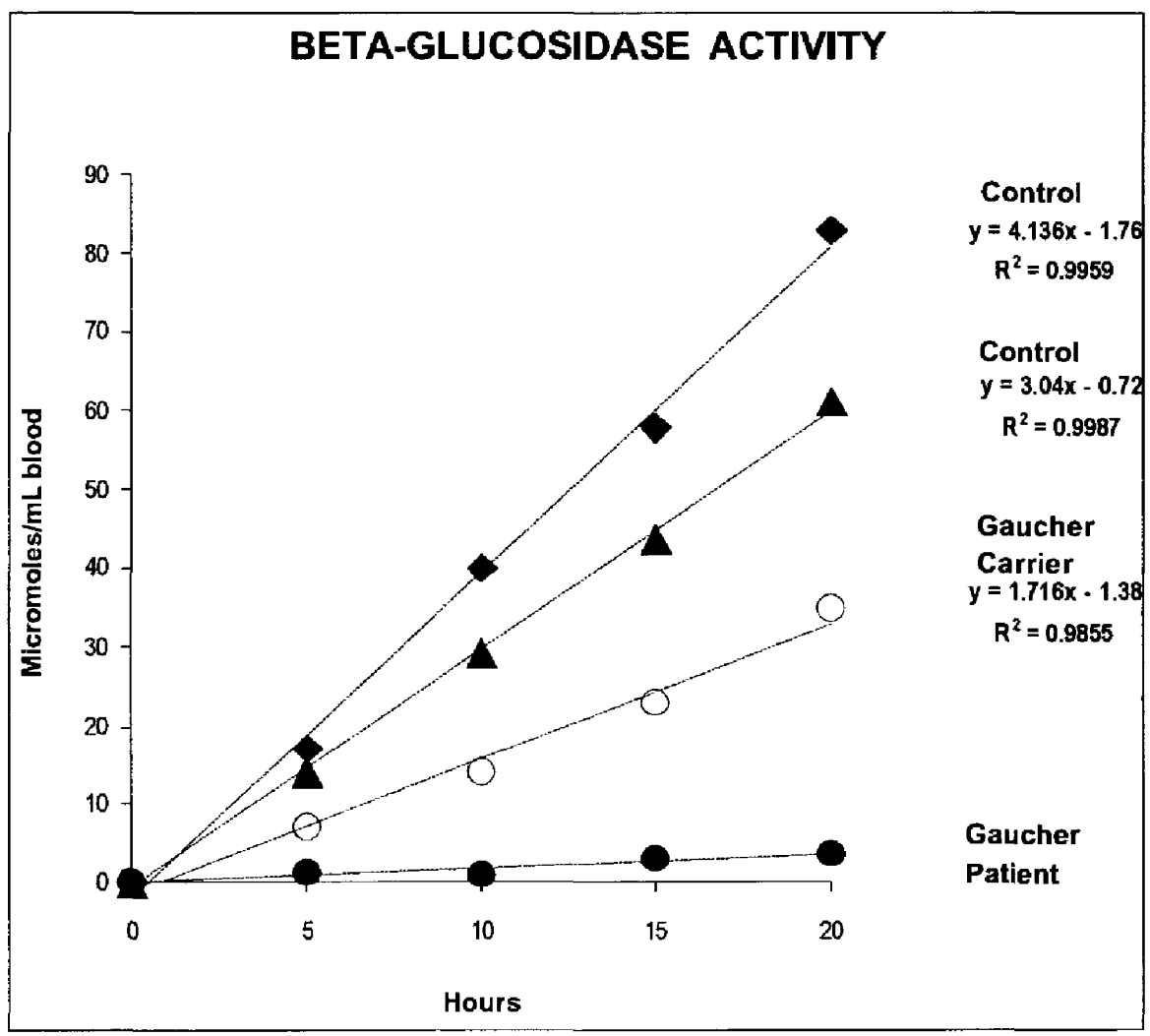
FIG. 3 illustrates the amount of hydrolyzed MU-β-D-glucopyranoside at variable incubation times. Each point represents the average of duplicate determinations.

FIG. 3 illustrates the amount of hydrolyzed MU-β-D-glucopyranoside at variable incubation times. In the Figure, the Controls represented by the square and triangular points refer to healthy adults and healthy newborns, respectively.

Table 3 shows the results obtained for Gaucher cases, Gaucher obligate carriers, healthy adults and newborns, sheep and mouse.

TABLE 3

| β-D-glucosidase activity (mmol/L blood/h) | |
|---|---|
| Gaucher disease type 1 (n = 50) Range | 0-0.63 |
| Gaucher obligate carrier (n = 23) Range | 0.98-2.07 |
| Healthy control (n = 60) Range | 1.40-3.06 |
| Healthy newborns (n = 45) Range | 1.73-6.06 |
| Sheep (n = 1) | 7.30 |
| Mouse (n = 3) | 23.0-35.9 |

EXAMPLE 7

Control of Gaucher Disease Treatment

Determination of Chitotriosidase Activity in Dried Blood Spots

A) To two 1-ml disposable test tubes the following were added sequentially:
   1) A 3 mm-diameter punch (5.5 µl of human blood) prepared according to the protocol indicated in Example 1,
   2) 20 µl of 0.25 M sodium acetate buffer (pH 5.5) as eluent, and
   3) 20 µl of 0.19 M MU-β-D-N,N',N" triacetylchitotrioside in distilled water as substrate.
B) The tests tubes were vigorously mixed by vortex (Vortexer Luckham, model V 400, USA) for 1 minute and then placed in a shaking water bath. The test tubes were incubated, one, for 10 minutes and the other, for 20 minutes. Both test tubes were incubated at 37° C.
C) After incubation, the tests tubes were placed in an ice bath, and 300 µl of 0.085 M glycine-sodium carbonate buffer (pH 10.5) were added to stop the reaction. The tests tubes were vortex mixed for 30 seconds (Coframo Ltd, Model Reax 2000, Ontario, Canada) and allowed to stand 30 minutes at room temperature.
D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate. The mean values for each 10-minute and 20-minute runs were calculated.

A blank sample was prepared according to the preceding protocol by incubating the substrate separately from the sample punch and the eluent. The substrate was added to the sample punch and the eluent after 3 hours. The reaction was immediately halted by adding 300 µl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed by utilizing ethylendiamine as stopping buffer.

Figure 4:
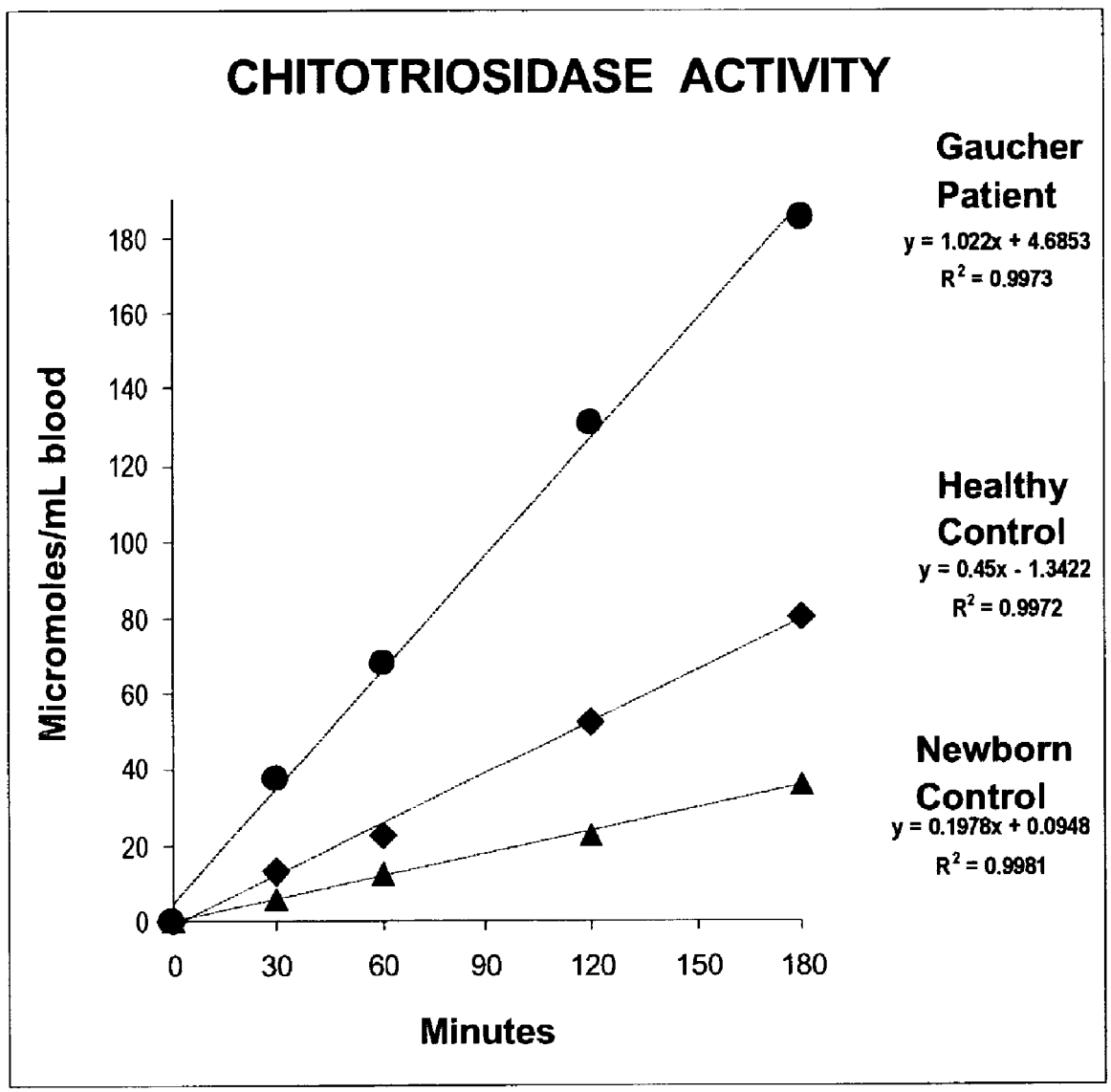
FIG. 4 illustrates the amount of hydrolyzed MU-β-D-N,N', N" triacetylchitotrioside at variable incubation times. Each point represents the average of duplicate determinations.

FIG. 4 illustrates the amount of hydrolyzed triacetylchitotrioside at variable incubation times.

Table 4 shows the results obtained for total, treated and untreated Gaucher cases, obligate carriers, healthy adults and newborns.

TABLE 4

| Chitotriosidase activity (mmol/L blood/h) | |
| --- | --- |
| Gaucher disease (n = 47) total Range | 17.0-702 |
| Gaucher disease (n = 26) treated Range | 17.0-299.5 |
| Gaucher disease (n = 21) untreated Range | 303.6-702.0 |
| Gaucher obligate carriers (n = 18) Range | 0-33.6 |
| Healthy adults (n = 65) Range | 0-29.0 |
| Healthy newborns (n = 53) Range | 0-33.2 |

EXAMPLE 8

Detection of Fabry Disease

Determination of α-D-galactosidase A Activity in Dried Blood Spots

A) To a 1-ml disposable test tube the following were added sequentially:
   1) A 3 mm-diameter punch (5.5 µl of human blood) prepared according to the protocol indicated in Example 1,
   2) 20 µl of 0.25 M N-acetyl-α-D-galactosamine in distilled water as eluent, and
   3) 50 µl of 5 mM MU-α-D-galactopyranoside in 0.15 M citrate-phosphate buffer (pH 4.4) as substrate.
B) The test tube was vigorously mixed by vortex (Vortexer Luckham, model V 400, USA) for 1 minute, placed then in a shaking water bath and incubated for 20 hours at 37° C.
C) After incubation, the test tube was placed in an ice bath, and 300 µl 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.
D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 µl of 0.085 M glycine-sodium carbonate buffer to the bank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with sheep and murine blood using the same protocol described above.

This assay was also performed by utilizing ethylendiamine as stopping buffer.

Figure 5:
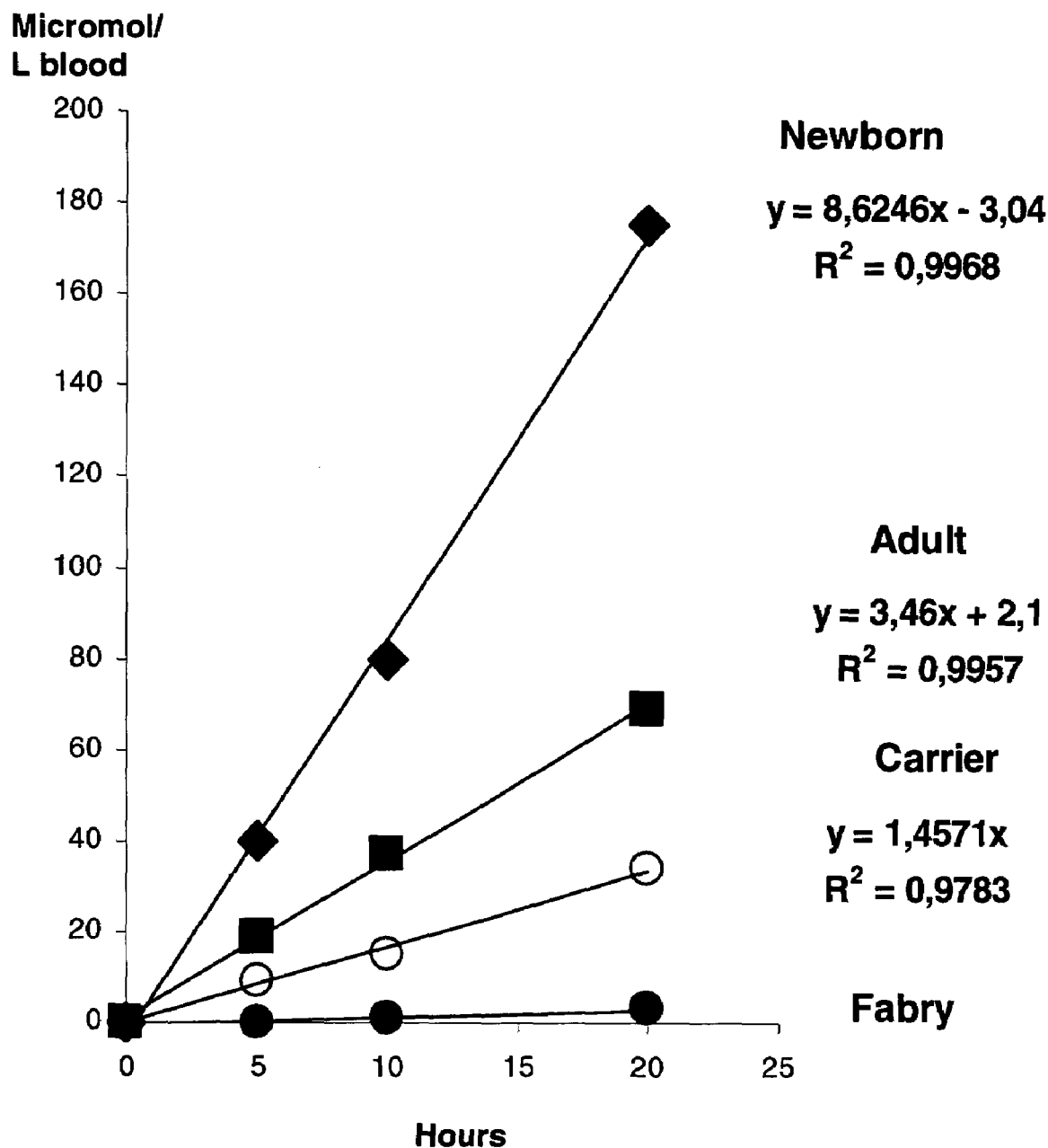
FIG. 5 illustrates the amount of hydrolyzed MU-α-D-galactopyranoside at variable incubation times. Each point represents the average of duplicate determinations.

FIG. 5 illustrates the amount of hydrolyzed MU-α-D-galactopyranoside at variable incubation times.

Table 5 shows the results obtained for Fabry cases, obligate carriers, healthy

TABLE 5

| α-galactosidase A activity (mmol/L blood/h) | |
| --- | --- |
| Fabry disease (n = 22) Range | 0-0.24 |
| Fabry obligate carriers (n = 11) Range | 0.67-2.94 |
| Healthy adults (n = 65) Range | 1.38-4.43 |
| Healthy newborns (n = 45) Range | 1.32-10.30 |
| Sheep (n = 1) | 3.76 |
| Mouse (n = 3) | 15.6-22.7 |

EXAMPLE 9

Detection of Sandhoff Disease and Mucolipidosis II/III

Determination of Total Hexosaminidase Activity in Dried Blood Spots

Patients with Sandhoff disease are identified by an acute deficiency of total hexosaminidase. As a contrast, patients with Mucolipidosis II/III are characterized by a high level of total hexosaminidase.

A) To a 1-ml disposable test tube the following were added sequentially:
  1) A 3 mm-diameter punch (5.5 µl of human blood) prepared according to the protocol indicated in Example 1,
  2) 50 µl of 0.022 M citrate-phosphate buffer (pH 4.4) as eluent, and
  3) 100 µl of 3 mM MU-2-acetamido-2-deoxy-β-D-glucopyranoside in 0.022 M citrate-phosphate buffer (pH 4.4) as substrate.

B) The test tube was vigorously mixed by vortex (Vortexer Luckham, model V 400, USA) for 1 minute, placed then in a shaking water bath and incubated for 2 hours at 37° C.

C) After incubation, the test tube was placed in an ice bath, and 300 µl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 1 hour. The reaction was immediately halted by adding 300 µl of 0.085 M glycine-sodium carbonate buffer to the blank sample. The fluorescence reading for the assayed sample was determined by subtracting the value of the blank sample to the enzyme product measurement. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with murine blood using the same protocol described above.

This assay was also performed by utilizing ethylendiamine as stopping buffer.

Figure 6:
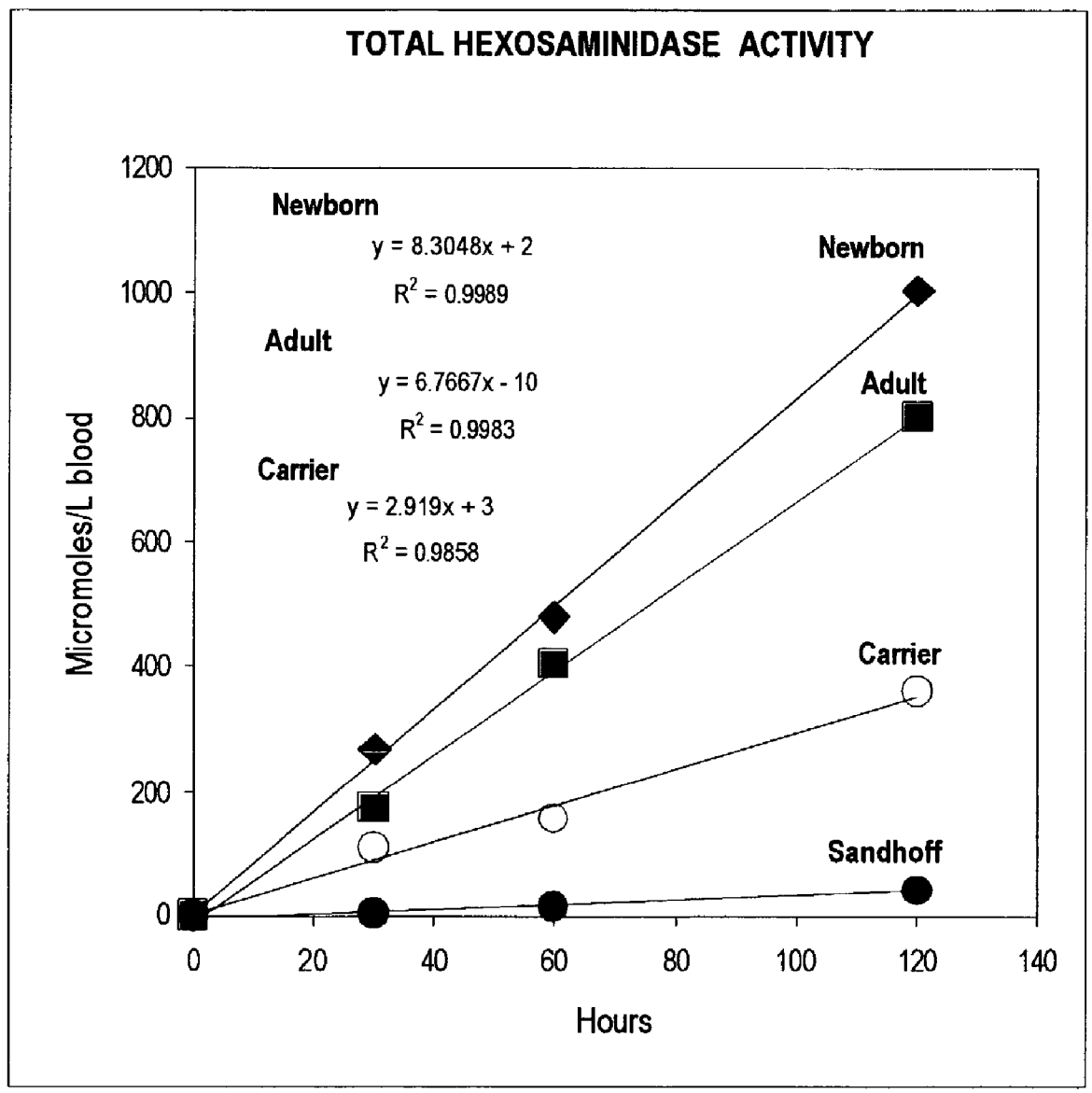
FIG. 6 illustrates the amount of hydrolyzed MU-2-acetamido-2-deoxy-β-D-glucopyranoside at variable incubation times. Each point represents the average of duplicate determinations.

FIG. 6 illustrates the amount of hydrolyzed MU-2-acetamido-2-deoxy-β-D-glucopyranoside at variable incubation times.

Table 6 shows the results obtained for Sandhoff cases, Mucolipidosis II/III cases, obligate carriers for both diseases, healthy adults and newborns and mouse.

TABLE 6

| | Total hexosaminidase activity (mmol/L blood/h) |
|---|---|
| Sandhoff disease (n = 3) Range | 16-57 |
| Sandhoff obligate carriers (n = 3) Range | 157-211 |
| Mucolipidosis II/III (n = 5) Range | 1,122-2,082 |
| Mucolipidosis II/III obligate carriers (n = 4) Range | 275-521 |
| Healthy adults (n = 50) Range | 240-472 |
| Healthy newborns (n = 30) Range | 362-672 |
| Mouse (n = 3) Range | 609-1,004 |

EXAMPLE 10

Detection of Tay-Sachs Disease

Determination of Hexosaminidase A Activity in Dried Blood Spots

A) To a 1-ml disposable test tube the following were added sequentially:
  1) A 3 mm-diameter punch (5.5 µl of human blood) prepared according to the protocol indicated in Example 1,
  2) 20 µl of distilled water, and
  3) 60 µl of 4 mM MU-N-acetyl-β-D-glucopyranoside sulfate in 0.022 M citrate-phosphate buffer (pH 4.4) as substrate.

B) The test tube was vigorously mixed by vortex (Vortexer Luckham, model V 400, USA) for 1 minute, placed then in a shaking water bath and incubated for 3 hours at 37° C.

C) After incubation, the test tube was placed in an ice bath, and 300 µl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 µl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed by utilizing ethylendiamine as stopping buffer.

Figure 7:
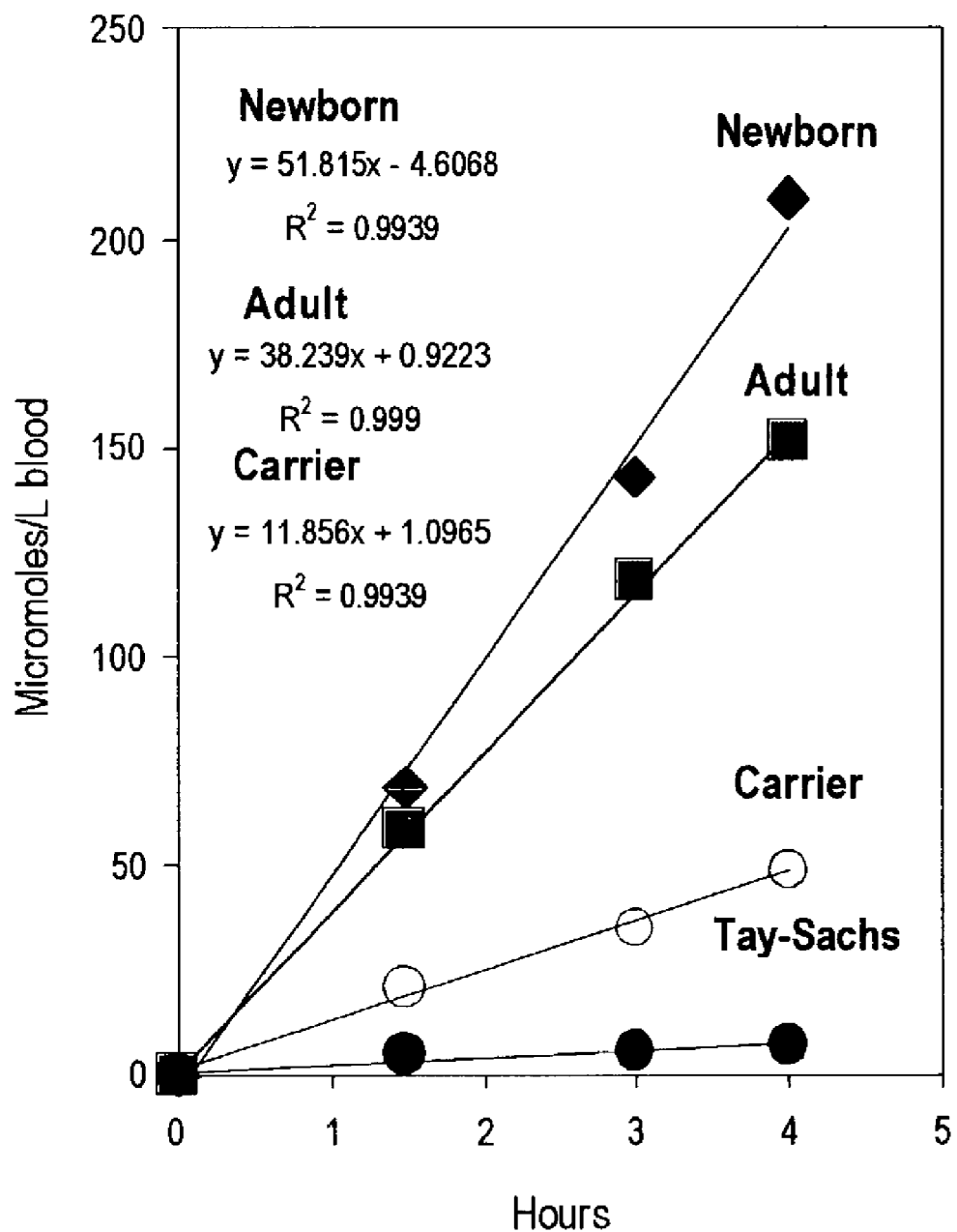
FIG. 7 illustrates the amount of hydrolyzed MU-N-acetyl-β-D-glucopyranoside sulfate at variable incubation times. Each point represents the average of duplicate determinations.

FIG. 7 illustrates the amount of hydrolyzed MU-N-acetyl-β-D-glucopyranoside sulfate at variable incubation times.

Table 7 shows the results obtained for Tay-Sachs cases, obligate carriers, healthy adults and newborns.

TABLE 7

| Hexosaminidase A activity (mmol/L blood/h) | |
| --- | --- |
| Tay-Sachs cases (n = 5) Range | 0.70-2.20 |
| Tay-Sachs obligate carriers (n = 8) Range | 11.3-22.2 |
| Healthy adults (n = 40) Range | 22.6-69.7 |
| Healthy newborns (n = 30) Range | 28.5-66.3 |

EXAMPLE 11

Detection of α-mannosidosis

Determination of α-D-mannosidase Activity in Dried Blood Spots

A) To a 1-ml disposable test tube the following were added sequentially:
1) A 3 mm-diameter punch (5.5 μl of human blood) prepared according to the protocol indicated in Example 1,
2) 30 μl of 0.17 M citrate-phosphate buffer (pH 4.4) containing 17.6 micrograms of zinc acetate as eluent, and
3) 50 μl of 0.8 mM MU-α-D-mannopyranoside in distilled water as substrate.

B) The test tube was vigorously mixed by vortex (Vortexer Luckham, model V 400, USA) for 1 minute, placed then in a shaking water bath and incubated for 2 hours at 37° C.

C) After incubation, the test tube was placed in an ice bath, and 300 μl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 2 hours. The reaction was immediately halted by adding 300 μl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with sheep and murine blood using the same protocol described above.

This assay was also performed by utilizing ethylendiamine as stopping buffer.

Table 8 shows the results obtained for α-Mannosidosis cases, obligate carriers, healthy adults and newborns and sheep and mouse.

TABLE 8

| α-D-mannosidase activity (inmmol/L blood/h) | |
| --- | --- |
| α-Mannosidosis cases (n = 2) Range | 4.7-5.8 |
| α-Mannosidosis obligate carriers (n = 1) Range | 18.5-37.3 |
| Healthy adults (n = 40) Range | 27.3-68.5 |
| Healthy newborns (n = 15) Range | 26.7-129.7 |
| Sheep (n = 1) | 203.0 |
| Mouse (n = 2) | 409.1-429.2 |

EXAMPLE 12

Detection of β-mannosidosis

Determination of β-D-mannosidase Activity in Dried blood Spots

A) To a 1-ml disposable test tube the following were added sequentially:
1) A 3 mm-diameter punch (5.5 μl of human blood) prepared according to the protocol indicated in Example 1,
2) 20 μl of distilled water as eluent, and
3) 100 μl of 1 mM MU-β-D-mannopyranoside in 0.1 M citrate-phosphate buffer (pH 4.5) as substrate.

B) The test tube was vigorously mixed by vortex (Vortexer Luckham, model V 400, USA) for 1 minute, placed then in a shaking water bath and incubated for 20 hours at 37° C.

C) After incubation, the test tube was placed in an ice bath, and 300 μl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 μl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with murine blood using the same protocol described above.

This assay was also performed by utilizing ethylendiamine as stopping buffer.

Figure 8:
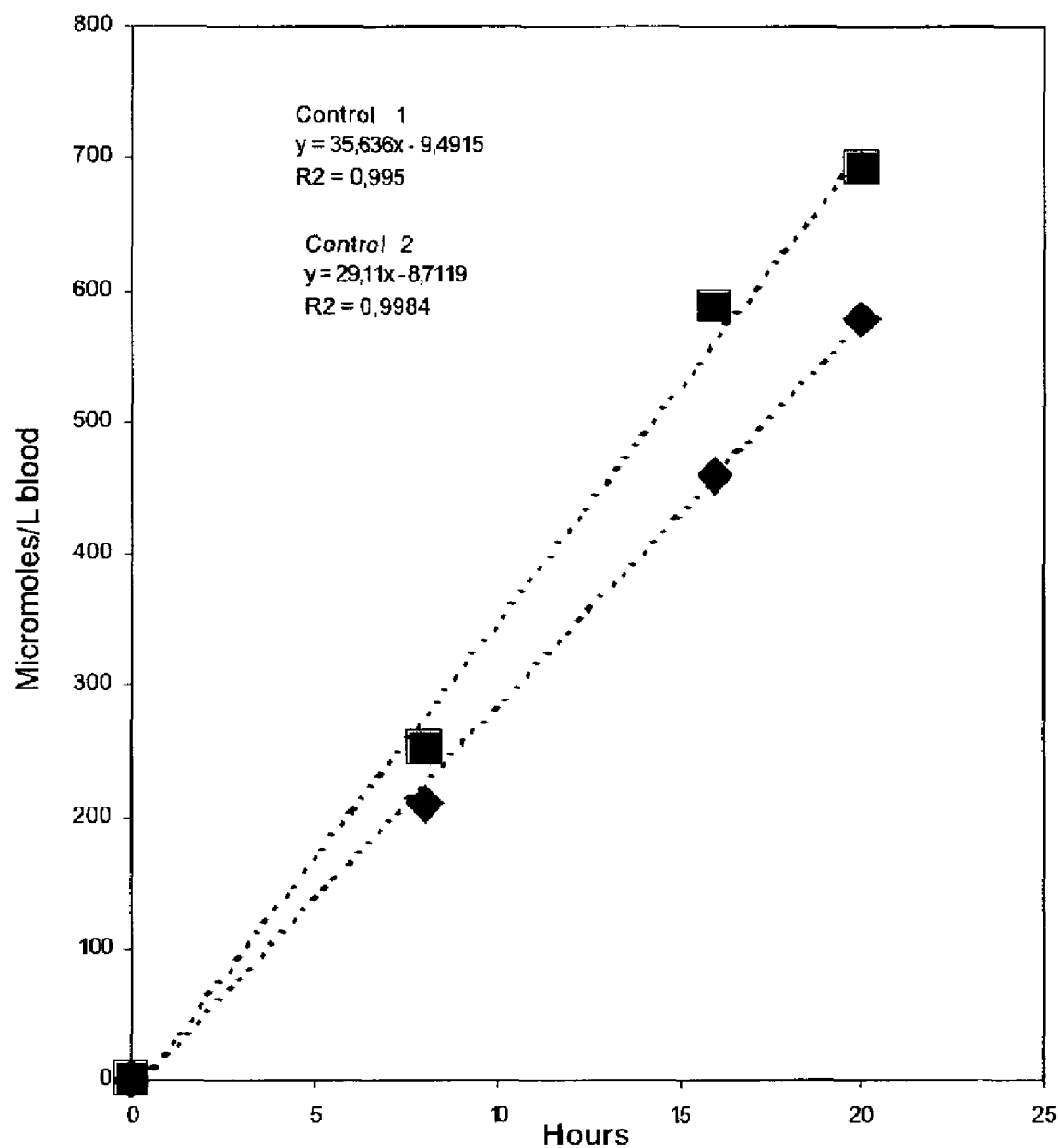
FIG. 8 illustrates the amount of hydrolyzed MU-β-D-mannopyranoside sulfate at variable incubation times. Each point represents the average of duplicate determinations.

FIG. 8 illustrates the amount of hydrolyzed MU-β-D-mannopyranoside sulfate at variable incubation times. In the Figure, the Controls represented by the larger and smaller square points refer to healthy adults and healthy newborns, respectively.

Table 9 shows the results obtained for healthy adults and mouse.

TABLE 9

| β-D-mannosidase activity (mmol/L blood/h) | |
|---|---|
| Healthy adults (n = 40) Range | 9.8-26.4 |
| Mouse (n = 2) Range | 136.9-209.5 |

EXAMPLE 13

Detection of α-fucosidosis

Determination of α-L-fucosidase Activity in Dried Blood Spots

A) To a 1-ml disposable test tube the following were added sequentially:
  1) A 3 mm-diameter punch (5.5 µl of human blood) prepared according to the protocol indicated in Example 1,
  2) 30 µl of 0.17 M citrate-phosphate buffer (pH 4.5) as eluent, and
  3) 50 µl of 1 mM MU-α-L-fucopyranoside in distilled water as substrate.
B) The test tube was vigorously mixed by vortex (Vortexer Luckham, model V 400, USA) for 1 minute, placed then in a shaking water bath and incubated for 16 hours at 37° C.
C) After incubation, the test tube was placed in an ice bath, and 300 µl of 0.085 M glycine-sodium carbonate buffer. (pH 10.5) were added to stop the reaction. The test tube was vortex mixed for 30 seconds (Coframo Ltd, Model Reax 2000, Ontario, Canada) and allowed to stand 30 minutes at room temperature.
D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 µl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with murine blood using the same protocol described above.

This assay was also performed by utilizing ethylendiamine as stopping buffer.

Figure 9:
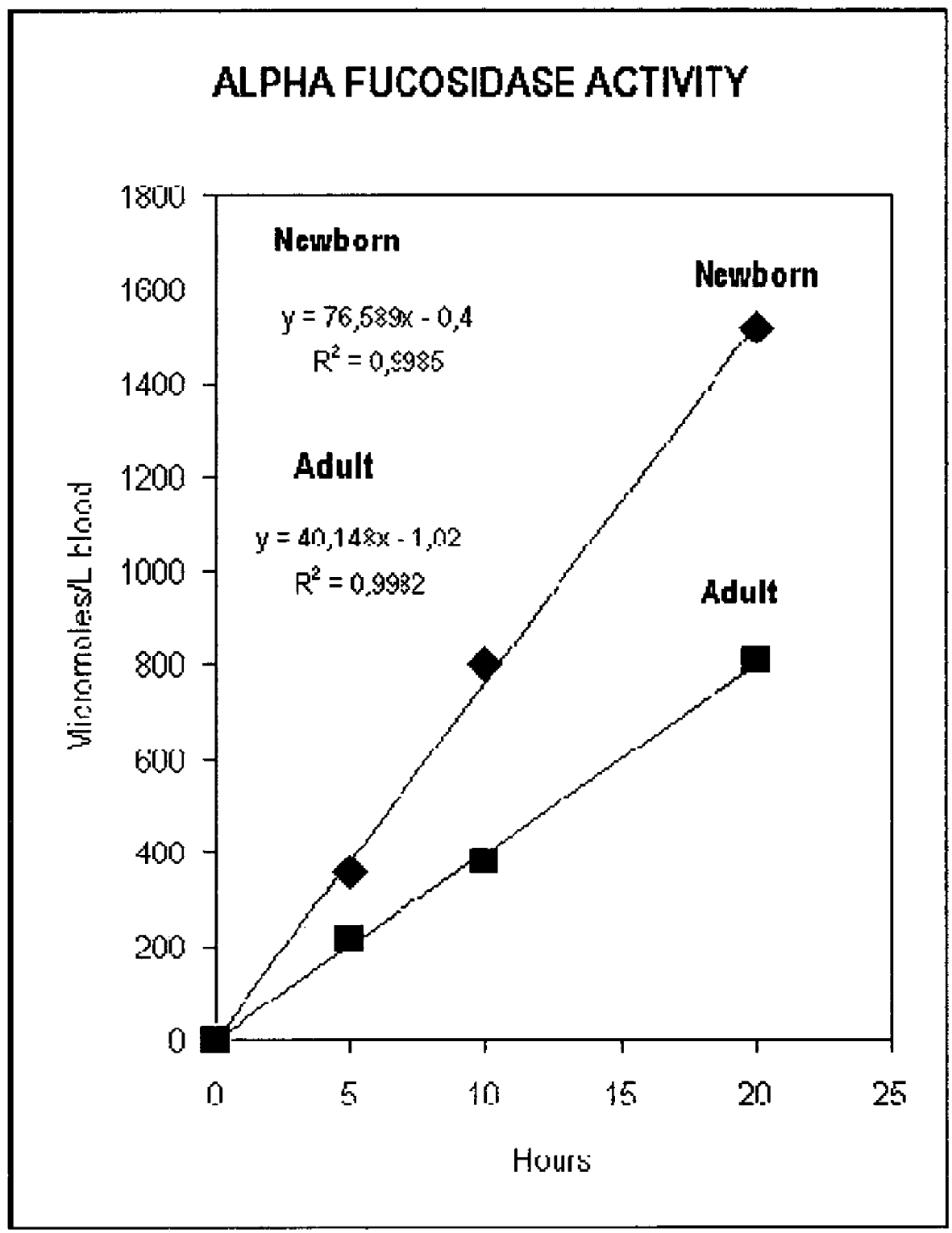
FIG. 9 illustrates the amount of hydrolyzed MU-α-L-fucopyranoside at variable incubation times. Each point represents the average of duplicate determinations.

FIG. 9 illustrates shows the amount of hydrolyzed MU-α-L-fucopyranoside at variable-incubation times.

Table 10 shows the results obtained for healthy adults and newborns.

TABLE 10

| α-L-fucosidase activity (mmol/L blood/h) | |
|---|---|
| Healthy adults (n = 40) Range | 13.3-53.9 |
| Healthy newborns (n = 15) Range | 18.0-72.1 |
| Mouse (n = 2) Range | 2.1-2.7 |

EXAMPLE 14

Detection of Schindler Disease

Determination of N-acetyl-α-galactosaminidase Activity in Dried blood Spots

A) To a 1-ml disposable test tube the following were added sequentially:
  1) A 3 mm-diameter punch (5.5 µl of human blood) prepared according to the protocol indicated in Example 1,
  2) 20 µl of distilled water as eluent, and
  3) 40 µl of 1 M MU-2-acetamido-2-deoxy-α-D-galactopyranoside in 0.2 M citrate-phosphate buffer (pH 4.7) as substrate.
B) The test tube was vigorously mixed by vortex (Vortexer Luckham, model V 400, USA) for 1 minute, placed then in a shaking water bath and incubated for 20 hours at 37° C.
C) After incubation, the test tube was placed in an ice bath, and 300 µl of 0.085 M glycine-sodium carbonate buffer (pH 10.5) were added to stop the reaction. The test tube was vortex mixed for 30 seconds (Coframo Ltd, Model Reax 2000, and Ontario, Canada) and allowed to stand 30 minutes at room temperature.
D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 µl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with murine blood using the same protocol described above.

This assay was also performed by utilizing ethylendiamine as stopping buffer.

Table 11 shows the results obtained for healthy adults and mouse.

TABLE 11

| N-acetyl-α-galactosaminidase activity (mmol/L blood/h) | |
|---|---|
| Healthy control (n = 25) Range | 2.80-7.90 |
| Mouse (n = 3) Range | 20.6-33.1 |

EXAMPLE 15

Detection of Maroteaux-Lamy Syndrome or MPS Type VI

Determination of Arylsutfatase B Activity in Dried Blood Spots

A) To a 1-ml disposable test tube the following were added sequentially:
  1) A 3 mm-diameter punch (5.5 µl of human blood) prepared according to the protocol indicated in Example 1,
  2) 30 µl of distilled water,
  3) 20 µl of 0.015 M lead acetate in 0.05 M sodium acetate buffer (pH 5.0) as eluent, and
  4) 50 µl of 10 mM MU-sulfate in 0.05 M sodium acetate buffer (pH 5.0) as substrate.
B) The test tube was vigorously mixed by vortex (Vortexer Luckham, model V 400, USA) for 1 minute, placed then in a shaking water bath and incubated for 20 hours at 37° C.
C) After incubation, the tube was placed in an ice bath, and 300 µl of 0.085 M glycine-sodium carbonate buffer (pH 10.5) were added to stop the reaction. The tube was vortex mixed for 30 seconds (Coframo Ltd, Model Reax 2000, Ontario, Canada) and allowed to stand 30 minutes at room temperature.
D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 µl of 0.085 M glycine-sodium carbonate buffer to the blank sample. The absorbance reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with sheep and murine blood using the same protocol described above.

This assay was also performed by utilizing ethylendiamine as stopping buffer. Table 12 shows the results obtained for MPS VI cases, a case of multiple sulfatase deficiency (MSD), obligate carriers for both diseases, healthy adults and newborns, sheep and mouse.

TABLE 12

| Arylsulfatase B activity (mmol/L blood/h) | |
|---|---|
| MPS VI cases (n = 11) Range | 0.65-1.76 |
| MPS VI obligate carriers (n = 8) Range | 2.90-5.73 |
| MSD case (n = 1) | 0.99 |
| MSD obligate carriers (n = 2) Range | 5.60-6.70 |
| Healthy adults (n = 50) Range | 3.78-14.61 |
| Healthy newborns (n = 35) Range | 5.9-26.3 |
| Sheep (n = 1) | 12.8 |
| Mouse (n = 3) | 31.3-64.4 |

EXAMPLE 16

Detection of Niemann-Pick Disease Type A and B

Determination of Sphingomyelinase Activity in Dried Blood Spots

1. Test Tube Preparation

To a 2-ml disposable test tube were added 20 µl of a 2:1 (v/v) chloroform:methanol solution containing 23.4 µg of sphingomyeline and 0.02 µCi $^{14}$C sphingomyeline as substrate. The substrate was dried by removing the organic solvent under a nitrogen atmosphere at room temperature.

2. Enzymatic Activity Determination by Radioactive Emission

A) To the 2-ml disposable test tube of the preceding step the following were added sequentially:
  1) 80 µl of distilled water containing 23 µg sodium taurocholate and 125 µg triton X-100,
  2) 20 µl of 2.5 M sodium acetate buffer (pH 5.0) as eluent, and
  3) a 3 mm-diameter punch (5.5 µl of human blood) prepared according to the protocol indicated in Example 1.
B) The test tube was vigorously mixed by vortex (Vortexer Luckham, model V 400, USA) for 3 minutes, placed then in a shaking water bath and incubated for 30 hours at 37° C.
C) The following protocol was performed sequentially with the test tube of the prior step:
  1) 100 µl of 10% bovine albumin in distilled water were added. The contents of the test tube were then vortex mixed gently for 10 seconds (Vortexer Luckham, model V 400, USA).
  2) 750 µl of 10% trichloroacetic acid were added. The contents of test tube were then vortex mixed for 30 seconds (Vortexer Luckham, model V 400, USA) and allowed to stand 5 minutes on ice.
D) The test tube was then centrifuged at 13,750 rpm for 5 minutes (Beckman Instruments, Microfuge E model, USA). 700 µl of the supernatant was removed and placed in a scintillation vial containing 3 ml of Ultima Gold-XR® (Packard Instrument Co). The radioactivity of the vial was counted during 5 minutes in a Tri-Carb Liquid Scintillation Analyzer (Packard Instrument Co, model 1900 TR, USA). The assay was done by duplicate.

Two blank test tubes were run for each assay. The blank test tubes were prepared according to the protocol described above omitting the punched filter paper. The radioactivity count for the blank samples should be 10 times less than the radioactivity counts for the assayed sample. If both blank samples complied with the acceptance criteria, their average was computed and compared with the assayed sample radioactive count. If only one blank sample complied with the acceptance criteria, only said value was compared with the assayed sample value. A second blank sample preparation was performed if both blank samples were rejected.

The dpm reading for the assayed sample was determined by subtracting the value of the dpm reading of the blank tubes to the dpm reading of the sample tube. The specific activity of the sample was calculated by comparing this result with the dpm/nmol of the substrate. The enzyme activity was expressed as dpm counted per ml of blood per hour.

This assay was also performed with murine blood using the same protocol described above.

Figure 10:
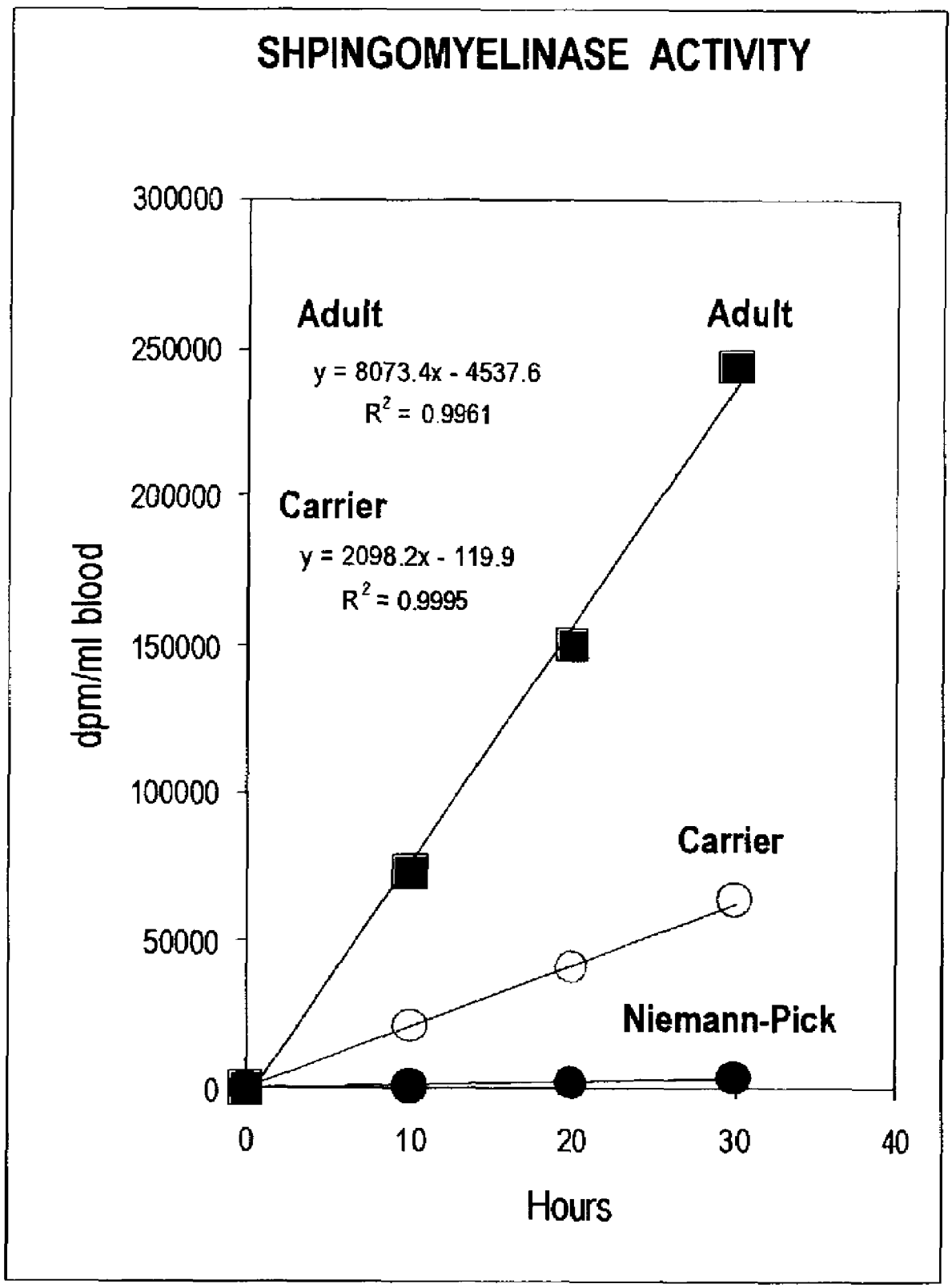
FIG. 10 illustrates the amount of $^{14}C$ sphingomyeline at variable incubation times. Each point represents the average of duplicate determinations.

FIG. 10 illustrates the amount of $^{14}C$ sphingomyeline at variable incubation times.

Table 13 illustrates the results obtained for Niemann-Pick type A/B cases, obligate carriers, healthy adults and newborns and mouse.

TABLE 13

Sphingomyelinase activity (dpm/ml blood/h)

| | |
|---|---|
| Niemann-Pick cases (n = 3) Range | 173-432 |
| Obligate carriers (n = 2) Range | 3,383-6,686 |
| Healthy adults (n = 15) Range | 4,261-11,134 |
| Healthy newborns (n = 17) Range | 1,507-7,710 |
| Mouse (n = 2) | 59,483-62,322 |

EXAMPLE 17

Detection of Krabbe Disease

Determination of β-galactocerebrosidase Activity in Dried blood Spots

1. Test Tube Preparation

To a 1-ml disposable test tube were added 20 μl of a 2:1 (v/v) chloroform:methanol solution, containing 0.5 mg sodium taurocholate, 15 μg oleic acid and 0.045 μCi $^3H$ galactosylceramide as substrate. The substrate was dried by removing the organic solvent under a nitrogen atmosphere at room temperature.

2. Enzymatic Activity Determination by Radioactive Emission

A) To the 1-ml disposable test tube of the preceding step the following were added sequentially:
   1) 100 μl of 0.05 M citrate-phosphate buffer (pH 4.1). The test tube contents were vigorously mixed by vortex (Vortexer Luckham, model V 400, USA) for 4 minutes and briefly sonicated (Heat Systems-Ultrasonics, Inc., model W225R, USA)
   2) A 3 mm-diameter punch (5.5 μl of human blood) prepared according to the protocol indicated in Example 1.
B) The test tube was vigorously mixed by vortex for 5 minutes, placed then placed in a shaking water bath and incubated for 20 hours at 37° C.
C) The test tube of the preceding step was placed in an ice bath and the following protocol was performed sequentially:
   1) 300 μl of a 1 mg/ml galactose solution in distilled water were added and vortex mixed for 10 seconds,
   2) 2.5 ml of a chloroform:methanol (2:1) solution were added and vortex mixed twice for 15 seconds.
D) The test tube was then centrifuged at 2,500 rpm for 10 minutes. 400 μl of the upper phase was removed and placed in a scintillation vial containing 3 ml of Ultima Gold-XR® (Packard Instrument Co). The radioactivity of the vial was counted during 5 minutes in a Tri-Carb Liquid Scintillation Analyzer (Packard Instrument Co, model 1900 TR, USA). The assay was done by duplicate.

Two blank test tubes were run for each assay. The blank test tubes were prepared according to the protocol described above omitting the punched filter paper. The radioactivity count for the blank samples should be 10 times less than the radioactivity counts for the assayed sample. If both blank samples complied with the acceptance criteria, their average was computed and compared with the assayed sample radioactive count. If only one blank sample complied with the acceptance criteria, only said value was compared with the assayed sample value. A second blank sample preparation was performed if both blank samples were rejected.

The dpm reading for the assayed sample was determined by subtracting the value of the dpm reading of the blank tube to the dpm reading of the sample. The specific activity of the sample was calculated by comparing this result with the cpm/nmol of the substrate. The enzyme activity was expressed as dpm counted per ml of blood per hour.

This assay was also performed with murine blood using the same protocol described above.

Table 14 illustrates the results obtained for Krabbe cases, obligate carriers, healthy adults and mouse.

TABLE 14

β-galactocerebrosidase activity (dpm/ml blood/h)

| | |
|---|---|
| Krabbe cases (n = 2) Range | 0 |
| Obligate carriers(n = 2) Range | 5,448-7,500 |
| Healthy adults (n = 15) Range | 6,471-15,682 |
| Mouse (n = 2) | 14,618-21,860 |

EXAMPLE 18

Detection of Hunter Disease or MPS Type II

Determination of Iduronate-2-sulfatase Activity in Dried Blood Spots

A) To a 2-ml disposable test tube the following were added sequentially:
   1) A 3 mm-diameter punch (5.5 μl of human blood) prepared according to the protocol indicated in Example 1 and 50 μl of 16 mM lead acetate in distilled water was added as eluent. The test tube was mixed gently 10 minutes at room temperature.
   2) 30 μl of substrate solution (Toronto Research Chemicals Inc., ON, Canada) was added. The substrate, tritiated iduronosyl sulfate anhydro-mannitol sulfate (7 μCi, 15.6 nmol) was reconstituted with 3.1 ml of a 0.33 M sodium acetate buffer (pH 4.5). The specific activity of the substrate is 450 mCi per mmol.
B) The test tube was mixed by vortex (Vortexer Luckham, model V 400, USA) for 30 seconds, placed then in a shaking water bath and incubated for 20 hours at 37° C.
C) After incubation, the test tube was placed in an ice bath, 1 ml of 10 mM sodium dibasic phosphate solution was added to stop the reaction.
D) The reaction mixture was applied to a small column (Pasteur pipette with a glass wool plug, containing 0.6 ml of a Cellex E in water). The column was rinsed with 2 ml of a 10 mM sodium dibasic phosphate solution.
E) 5 ml of a freshly prepared 70 mM sodium formate solution was added and the eluate was placed in a scintillation vial containing 15 ml of Opti-fluor® (Packard Instrument Co). The radioactivity of the vial was counted during 5 minutes in a Tri-Carb Liquid Scintillation Analyzer (Packard Instrument Co, model 1900 TR, USA). The assay was done by duplicate.

Two blank test tubes were run for each assay. The blank test tubes were prepared according to the protocol described above omitting the punched filter paper.

The dpm reading for the assayed sample was determined by subtracting the value of the dpm reading of the blank tube to the dpm reading of the sample. The activity of the sample was calculated by comparing this result with the dpm/nmol of the substrate. The enzyme activity was expressed as nanomoles per liter of blood per hour.

Table 15 illustrates the results obtained for MPS type II cases, a case of MSD, obligate carriers for both diseases, healthy adults and newborns.

TABLE 15

| Iduronate-2-sulfatase activity (nmol/L blood/h) | |
| --- | --- |
| MPS II cases (n = 11) Range | 0-12 |
| MPS II obligate carriers (n = 10) Range | 40-104 |
| MSD disease (n = 1) | 0 |
| MSD obligate carriers (n = 2) Range | 80-96 |
| Healthy adults (n = 20) Range | 77-181 |
| Healthy newborns (n = 12) Range | 134-311 |

EXAMPLE 19

Detection of MPS type VII or Sly Syndrome

Determination of β-D-glucuronidase Activity in Dried Blood Spots

MPS type VII or Sly syndrome was detected by measuring the β-D-glucuronidase activity with a fluorogenic and a photometric substrate.

1. Enzymatic Activity Determination by Fluorogenic Analysis
   A) To a 1-ml disposable test tube the following were added sequentially:
      1) 3 mm-diameter punch (5.5 μl of human blood) prepared according to the protocol indicated in Example 1,
      2) 50 μl of distilled water as eluent, and
      3) 50 μl of 10 mM MU-β-D-glucuronic acid in 0.1 M sodium acetate buffer (pH 4.8) as substrate.
   B) The test tube was vigorously mixed by vortex (Vortexer Luckham, model V 400, USA) for 1 minute, placed then in a shaking water bath and incubated for 4 hours at 37° C.
   C) After incubation, the tube was placed in an ice bath, and 300 μl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.
   D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 4 hours. The reaction was immediately halted by adding 300 μl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. Enzyme activity was expressed as micromoles of hydrolyzed substrate per liter of blood per hour.

This assay was also performed with murine blood using the same protocol described above.

This assay was also performed by utilizing ethylendiamine as stopping buffer.

Table 16a shows the results obtained for MPS type VII cases, obligate carriers, healthy adults and newborns and mouse.

TABLE 16a

| β-glucuronidase activity (mmol/L blood/h) | |
| --- | --- |
| MPS VII cases (n = 2) Range | 0 |
| MPS VII obligate carrier (n = 1) | 53.6 |
| Healthy adults (n = 50) Range | 33.6-134.6 |
| Healthy newborns (n = 22) Range | 86.2-279 |
| Mouse (n = 3) | 82.4-144.5 |

2. Enzyme Activity Determination by Spectrophotometric Analysis
   A) To a 1-ml disposable test tube the following were added sequentially:
      1) A 3 mm-diameter punch (5.5 μl of human blood) prepared according to the protocol indicated in Example 1,
      2) 60 μl of 0.083 M sodium acetate buffer (pH 5.0) as eluent, and 3) 50 μl of 10 mM phenolphthalein-β-D-glucuronic acid in distilled water as substrate.
   B) The test tube was vigorously mixed by vortex (Vortexer Luckham, model V 400, USA) for 1 minute, placed then in a shaking water bath and incubated for 20 hours at 37° C.
   C) After incubation, the test tube was placed in an ice bath, and 300 μl of 0.1 M sodium hydroxide were added to stop the reaction. The test tube was vortex mixed for 30 seconds (Coframo Ltd, Model Reax 2000, Ontario, Canada) and allowed to stand 30 minutes at room temperature.
   D) Absorbance was determined on an Eppendorf photometer (Hinz GmbH, Eppendorf GN, Germany) at a wavelength of 550 nm using water as reference. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 μl of 0.1 M sodium hydroxide to the blank sample. The absorbance reading for the assayed sample was determined by subtracting the value of the blank sample to the enzyme product value. This result was compared to a calibration curve of absorbance values versus phenolphthalein concentrations to calculate the amount of hydrolyzed substrate and determine the enzyme activity value. Enzyme activity was expressed as micromoles of hydrolyzed substrate per liter of blood per hour.

This assay was also performed with sheep, and murine blood using the same protocol described above.

This assay was also performed by utilizing ethylendiamine as stopping buffer.

Table 16b shows the results obtained for healthy adults, sheep and mouse.

TABLE 16b

| β-glucuronidase activity (mmol/L blood/h) | |
| --- | --- |
| Healthy control (n = 2) Range | 21.6-45.6 |
| Sheep (n = 1) Range | 21.4 |
| Mouse (n = 1) Range | 59.3 |

EXAMPLE 20

Determination of α-L-iduronidase Activity in Dried Chorionic Villae and Cultured Amniocytes Samples A) To a 1-ml disposable test tube the following were added sequentially:
1) A 3 mm-diameter punch dried chorionic villae prepared according to the protocol indicated in Example 2,
2) 40 μl of 0.05 M sodium formate buffer (pH 2.8) containing 0.3 μg of D-saccharic acid-1,4-lactone as eluent, and
3) 20 μl of 2 mM MU-α-L-iduronide in distilled water as substrate.

B) The test tube was vigorously mixed by vortex (Vortexer Luckham, model V 400, USA) for 5 minutes, placed then in a shaking water bath and incubated for 20 hours at 37° C.

C) After incubation, the test tube was placed in an ice bath, and 300 μl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 μl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. The enzyme activity value was related to the protein concentration of the sample, previously measured by the Lowry method. The enzyme activity was expressed as nanomoles of hydrolyzed substrate per mg of protein per hour.

The protocol described above was repeated utilizing dried amniocytes samples prepared according to Example 3 obtained from pregnant women as α-iduronidase source.

This assay was also performed by utilizing ethylendiamine as stopping buffer.

Table 17 shows the results obtained for a chorionic villae sample from a healthy woman 13 weeks pregnant. Table 16 also shows the results for cultured amniocytes samples from two healthy women 19 and 20 weeks pregnant.

TABLE 17

| α-L-iduronidase activity (nmoles/mg protein/h) | |
| --- | --- |
| Chorionic villae | 2.86 |
| Cultured amniocytes, Sample 1 | 7.64 |
| Cultured amniocytes, Sample 2 | 3.79 |

EXAMPLE 21

Determination of Total Hexosaminidase Activity in Dried Chorionic Villae Samples A) To a 1-ml disposable test tube the following were added sequentially:
1) A 3 mm-diameter punch dried chorionic villae prepared according to the protocol indicated in Example 2,
2) 50 μl of 0.022 M citrate-phosphate buffer (pH 4.4) as eluent, and
3) 100 μl of 3 mM MU-2-acetamido-2-deoxy-β-D-glucopyranoside in 0.022 M citrate-phosphate buffer (pH 4.4) as substrate.

B) The test tube was vigorously mixed by vortex (Vortexer Luckham, model V 400, USA) for 1 minute, placed then in a shaking water bath and incubated for 2 hours at 37° C.

C) After incubation, the test tube was placed in an ice bath, and 300 μl of 0.085 M glycine-sodium carbonate buffer (pH 10.5) were added to stop the reaction. The test tube was vortex mixed for 30 seconds (Coframo Ltd, Model Reax 2000, Ontario, Canada) and allowed to stand 30 minutes at room temperature.

D) The fluorescence of the enzyme product 4-methylumbelliferone was measured on a Farrand fluorometer Model RF-2 (Farrand Optical Inc. NY, USA). The measurement was performed in a quartz cell, at an excitation wavelength of 365 nm and an emission wavelength of 450 nm. The assay was done by duplicate.

A blank sample was prepared according to the preceding protocol by incubating the substrate separately from the sample punch and the eluent. The substrate was added to the sample punch and the eluent after 20 hours. The reaction was immediately halted by adding 300 μl of 0.085 M glycine-sodium carbonate buffer to the blank sample. The fluorescence reading for the assayed sample was determined by subtracting the value of the blank sample to the enzyme product value. This result was compared to a standard 4-methylumbelliferone solution to calculate the amount of hydrolyzed substrate and determine the enzyme activity value. The enzyme activity value was related to the protein concentration of the sample, previously measured by the Lowry method. The enzyme activity was expressed as nanomoles of hydrolyzed substrate per mg of protein per hour.

This assay was also performed by utilizing ethylendiamine as stopping buffer.

Table 18 shows the result obtained for a chorionic villae sample from a healthy woman 13 weeks pregnant.

TABLE 18

| Total hexosaminidase activity (nmoles/mg protein/h) | |
| --- | --- |
| Chorionic villae | 120.8 |

EXAMPLE 22

Medium Term Stability of Lysosomal Enzyme Activities on Dried Blood Spots

Twenty samples of dried blood prepared according to the protocol described Example 1 were stored for 20 and 40 days at 4° C. and 25° C. At 20 and 40 days the samples were assayed to determine the enzymatic activities of α-L-iduronidase and β-D-galactosidase according to the protocols described in Examples 4 and 5, respectively. These enzymes were selected particularly to cover the widest stability range of lysosomal enzymes: α-L-iduronidase and β-D-galactosidase are described in the art as showing respectively, one of the lowest and one of the highest stability values for lysosomal enzymes.

Blood samples were collected from a GM1 gangliosidosis or MPS type I patient and healthy controls to determine the activity of α-L-iduronidase. The β-D-galactosidase activity assay was performed in healthy controls. Enzyme activities were assayed on day 1 (baseline) and after 20 and 40 days of storage at the indicated temperatures. The average values of all measurements for each group, temperature and storage time were computed.

Table 19a shows the changes of the β-D-galactosidase activity in dried blood stored at 4° C. and 25° C. The activity of β-D-galactosidase after 20 and 40 days of storage at 4° C. did not differed significantly from the baseline value. Enzyme activity values for β-D-galactosidase declined mildly after 20 and 40 days of storage at 25° C. The activity decreased by 10.2% and 42.6% from the baseline value for samples stored at 4° C. and 25° C., respectively.

Table 19b shows the changes of the α-L-iduronidase activity in dried blood stored at 4° C. and 25° C. The activity of α-L-iduronidase after 20 and 40 days of storage at 4° C. did not differed significantly from the baseline value. Enzyme activity values for α-L-iduronidase declined slightly after 40 days of storage at 25° C.: the activity present at that time represented the 85.8% of the baseline value. After 20 and 40 days of storage at 25° C. the α-L-iduronidase activity decreased by 31.9% and 59.3% from the baseline value, respectively.

TABLE 19a

β-D-galactosidase activity stability at 4° C. and 25° C.

| Days | 4° C. | | 25° C. | |
|---|---|---|---|---|
| Sample | Control | GM1 Case | Control | GM1 Case |
| Basal | 53.2 | 2.1 | 53.2 | 2.1 |
| 20 | 54.1 | 1 | 47.8 | 0 |
| 40 | 52 | 0 | 36 | 0 |

TABLE 19b

α-L-iduronidase activity stability at 4° C. and 25° C. nmoles/ml blood/20 hs

| Days | 4° C. | | 25° C. | |
|---|---|---|---|---|
| Sample | Control | GM1 Case | Control | GM1 Case |
| Basal | 60.4 | 0 | 69.4 | 0 |
| 20 | 64.8 | 0 | 47.3 | 0 |
| 40 | 59.6 | 0 | 28.3 | 0 |

EXAMPLE 23

Lysosomal Enzyme Activity Assay Long Term Diagnostic Reliability and Long Term Stability of Lysosomal Enzyme Activities on Dried Blood Spots The reliability of the claimed assay to determine the activity of lysosomal enzymes present in samples stored for long periods of time under adverse environmental conditions was evaluated according to the following protocol:

Dried blood spots obtained from newborn screening cards (NSCs) stored at room temperature (RT) for varying periods of time were recovered for LSDs cases and healthy newborns. The LSDs cases included individuals affected MPS I, GM1 gangliosidosis, Gaucher, Sandhoff, Tay-Sachs and Niemann-Pick type B diseases. For each LSD case, three NSCs from healthy newborns delivered at approximately the same time were recovered for comparison. All samples were prepared according to the protocol described in Example 1.

Each group of samples (LSD case and three controls) was assayed according to the applicable preceding examples to determine the activity of deficient lysosomal enzyme. Determination of α-L-iduronidase, β-D-galactosidase, β-D-glucosidase, total hexosaminidase, hexosaminidase A and sphingomyelinase activities in dried blood spots were performed according to the protocols described in Examples 4, 5, 6, 9, 10 and 16, respectively.

Table 20 shows the enzymatic activity from LSDs cases and controls, and the storage time for each group of samples. The enzymatic activity was expressed as percentage of the mean activity of the healthy newborns enzymatic activity.

Enzyme activity values on healthy newborns declined on storage at room temperature, but regardless of this declination, the sample of each case could be clearly distinguished from healthy newborn samples stored at the same date. This difference was clearly visualized on samples stored up to 50 months, making feasible the retrospective screening of LSDs in dried blood spots samples.

TABLE 20

Activities of lysosomal enzymes stored for long periods of time at room temperature

| Disease | Enzyme assayed | Storage time at RT | LSD Case (n = 1) % of activity | Healthy Newborns (n = 3) Range % of activity |
|---|---|---|---|---|
| MPS I | α-L-iduronidase | 50 months | 7 | 40-60 |
| GM1 Gangliosidosis | β-D-galactosidase | 15 months | 5 | 52-66 |
| Gaucher | β-D-glucosidase | 15 months | 4 | 61-67 |
| Sandhoff | Total hexosaminidase | 20 months | 3 | 51-80 |
| Tay-Sachs | Hexosaminidase A | 36 months | 5 | 71-86 |
| Niemann-Pick | Sphingomyelinase | 16 months | 8 | 65-72 |

EXAMPLE 24

Diagnostic Kit for Determining the Activity of β-D-galactosidase

1. Kit Elements

A diagnostic kit for determining the activity of β-D-galactosidase according to the protocol described in Example 5 was prepared containing the following elements necessary for 100 determinations:

A first container containing 5 ml of a 0.45% (w/v) sodium chloride solution prepared in 0.05 M citrate-phosphate buffer (pH 4.4) as eluent and incubation buffer, A second container containing 200 nanomoles of MU-β-D-galactopyranoside as substrate, A third container containing 10 ml of distilled water as diluent, A fourth container containing 37.5 ml of a 0.085 M glycine-sodium carbonate buffer (pH 10.5) as stopping buffer, A fifth container containing 200 nanomoles of 4-methylumbelliferone to be used as fluorescence standard for calculating the amount of enzyme product produced, A first plastic bag containing a sample proceeding from a healthy individual to be used as high enzyme activity control, A second plastic bag containing a sample proceeding from a GM1 patient to be used as low enzyme activity control, and 110 test tubes to perform the enzyme activity determination.

An assay was performed according to the protocol described in Example 5 utilizing the kit described above. The results obtained were comparable to the results revealed in Example 5. Multiwell plates were also utilized to perform the assay in lieu of a test tube.

2. Technical Considerations

The substrate solution was prepared by adding the necessary quantity of distilled water and mixing vigorously. This step was done immediately before use. The substrate solution could be stored for up to one week at 4° C. without reducing noticeably their reactive capacity. Buffer solutions and distilled water could be stored at room temperature for a maximum of six months without reducing noticeably their reactive capacity.

Due to the chemical instability of the substrate (MU-β-D-galactopyranoside) and the fluorescence standard (4-methylumbelliferone) in water, these reagents should be kept in dark room and prepared immediately before use.

Dried samples from healthy individuals were used as high enzyme activity control, and dried samples from GM1 cases were used as low enzyme activity control. It is recommended the control samples be dried because in this form they are more stable. Control samples may be from animal origin or recombinant proteins.

Multiwell plates previously coated with the substrate may also be utilized to perform the assay instead of preparing the substrate solution separately.

Finally, some nonessential elements like filter paper and a punching system may be added to the diagnostic kit for further convenience.

All publications mentioned hereinabove are hereby incorporated in their entirety by reference.

While the foregoing invention has been described in some detail for purposes of clarity and understanding, it will be appreciated by one skilled in the art from a reading of this disclosure that various changes in form and detail can be made without departing from the true scope of the invention and appended claims.

REFERENCES

Dean, K. J. et al., "Fabry disease," *Practical Enzymology of the Sphingolipidoses*, R. H. Glew and S. P. Peters, Eds., Alan R. Liss, Inc. NY, pp. 173-216 (1977).

Den Tandt, W. R. et al., "Plasma methylumbelliferyl-tetra-N-acetyl-β-D-chitotetraoside hydrolase as a parameter during treatment of Gaucher patients," *Biochem. Mol. Med.* 57:71-72 (1996).

Fishman, W. K, "Human serum β-glucuronidase," *Clin. Chim. Acta* 15:435 (1967).

Grabowski G. A. Etal., "Enzyme therapy for gaucher disease: the first 5 years," *Blood Reviews* 12:115-133 (1998).

Ida H. et al., "Effect of enzyme replacement therapy or BMT in 16 japanese pediatric patients with Gaucher disease," *Abstracts of the Joint Meeting of International Symposium on Innovative Therapies & 6th International Symposium on Mucopolysaccharidosis & Related Diseases*, May 19-21, 2000, Minneapolis, Minn., USA.

Hopwood J. J. et al., "Long-term clinical progress in bone marrow transplanted mucopolysaccharidosis type I patients with a defined genotype," *J. Inherit. Metab. Dis.* 16(6):1024-33 (1993).

Hopwood et al., "Diagnosis of lysosomal storage disorders: evaluation of lysosome-associated membrane protein LAMP-1 as a diagnostic marker," *Clinical Chem.* 45(8): 1325-1335 (1997).

Kakkis E. D et al., "Enzyme replacement therapy in MPS I: current status of patients up to 104 weeks of therapy," *Abstracts of the Joint Meeting of International Symposium on Innovative Therapies & 6th International Symposium on Mucopolysaccharidosis & Related Diseases*, May 19-21, 2000, Minneapolis, Minn., USA.

Lowry et al., "Protein measurement with the Folin reagent," *J. Biol. Chem.* 193:265-275 (1951).

Mayes, J. S. et al., "Differential assay for lysosomal alpha galactosidases in human tissue and its application to Fabry's disease," *Clin. Chim. Acta* 112:247-251 (1981). Krivit, W. et al., "Bone marrow transplantation for globoid cell leukodystrophy, adrenoleukodystrophy, metachromatic leukodystrophy, and Hurler syndrome," *Curr. Opin. Hematol.* 6(6):377-82 (1999).

Meikle P. J. et al., "Prevalence of lysosomal storage disorders," JAMA 281-:249-254 (1999).

Rodriguezsema, M. et al., "Angiokeratoma corporis diffusum associated with beta-mannosidase deficiency," *Arch. Dermat.* 132:1219-1222 (1996).

Schiffmann, R., et al., "Infusion of (x-D-galactosidase A reduces tissue globotriaosylceramide storage in patients with Fabry disease," *J. Clin. Invest.* 97:365-370 (2000).

Singer et al., "Hexosaminidase A in tears and in saliva for rapid identification of Tay-Sachs disease and its carriers," *Lancet* 2:1116 (1973).

Vellodi, A. et al., "Allogenic bone marrow transplantation for fucosidosis," *Bone Marrow Transplan.* 15:153-158 (1995).

Wenger D. A. et al., "Screening for lysosomal disorders," *Techniques in Diagnostic Human Biochemical Genetics, A Laboratory Manual*, F. A. Hommes, Ed., Wiley-Liss, Inc. New York, NY, pp. 587-617 (1961).

Willems, P. J. et al., "Fucosidosis revisited: a review of 77 patients," *Am. J. Med. Genet.* 38:111-131 (1991).

Young, E. et al., "Plasma chitotriosidase activity in Gaucher disease patients who have been treated either by bone marrow transplantation or by enzyme replacement therapy with alglucerase," *J. Inherit. Metab. Dis.* 20(4):595-602 (1997).

What is claimed is:

1. A method for assaying the activity of a lysosomal enzyme selected from the group consisting of α-L-iduronidase, β-D-galactosidase, β-D-glucosidase, α-D-galactosidase A, total hexosaminidase, hexosaminidase A, arylsulfatase B, sphingomyelinase and iduronate-2-sulfatase present in a dried blood spot, said method comprising: (a) placing blood on a porous surface material and drying to form a dried blood spot, (b) combining the dried blood spot with (1) an eluent, (2) an incubation buffer and (3) at least one substrate capable of reacting with said lysosomal enzyme and generating at least one enzyme product, to form an incubation media; (c) incubating said media under conditions sufficient to generate said enzyme product; and (d) measuring said enzyme product to determine the activity of said lysosomal enzyme.

2. The method according to claim 1 wherein said dried blood spot is of mammalian origin.

3. The method according to claim 2 wherein said mammalian origin dried blood spot comprises a dried blood spot of sheep, mouse, or human origin.

4. The method according to claim 3 wherein said mammalian origin dried blood spot is human.

5. The method according to claim 1 wherein said porous surface material comprises filter paper.

6. The method according to claim 1 wherein said eluent, incubation buffer and substrate(s) in step (a) are added sequentially to said dried blood spot in the order (1), (2) and (3).

7. The method according to claim 1 wherein said eluent comprises water, sodium taurocholate, sodium chloride, citrate-phosphate buffer, sodium acetate, lead acetate, TRITON™X-100, D-saccharic acid-1,4-lactone, or mixtures thereof.

8. The method according to claim 1 wherein said incubation buffer has a pH value of less than 7.

9. The method according to claim 8 wherein said incubation buffer has a pH value of less than 5.5.

10. The method according to claim 1, wherein said incubation buffer comprises sodium formate, sodium citrate, sodium phosphate, sodium acetate, or mixtures thereof.

11. The method according to claim 1 wherein said substrate(s) comprise(s) at least one type of molecule capable of being converted by a lysosomal enzyme.

12. The method according to claim 11 wherein said type of molecules comprises 4-methylumbelliferyl-a-L-iduronide, 4-methylumbelliferyl-13-D-galactoside, 4-methylumbelliferyl-13-D-glucuronic acid, 4-methylumbelliferyl-a-D-galactoside, 4-methylumbelliferyl-13-D-galactopyranoside, 4-methylumbelliferyl-a-D-galactopyranoside, 4-methylumbelliferyl-13-N-N'-N" triacetylchitotrioside, 4-methylumbelliferyl-sulfate, 4-methylumbelliferyl-2-acetamido-2-deoxy-13-D-glucopyranoside, 4-methylumbelliferyl-N-acetyl-β-D-glucopyranoside, or mixtures thereof.

13. The method according to claim 1 wherein said substrate(s) comprise(s) natural molecules, synthetic molecules, or mixtures thereof.

14. The method according to claim 1 wherein said substrate(s) comprises a fluorophoric moiety.

15. The method according to claim 14 wherein said fluorophoric moiety comprises 4-methyllumbelliferyl.

16. The method according to claim 1 wherein substrate(s) comprise(s) a chromophoric moiety.

17. The method according to claim 16 wherein said chromophoric moiety comprises 4-nitrocatechol or phenolphthalein.

18. The method according to claim 1 wherein said substrate(s) comprises a radioactive moiety.

19. The method according to claim 18 wherein said radioactive moiety comprises $^{14}C$ sphingomyelin or $^{3}H$ galactosylceramide.

20. The method according to claim 1 wherein in step (c), said conditions sufficient to generate said enzyme product comprises a time of between 24 and 48 hours.

21. The method according to claim 1 wherein in step (b) said conditions sufficient to generate said enzyme product comprises a time of less than 24 hours.

22. The method according to claim 1 wherein in step (b), said conditions sufficient to generate said enzyme product comprises a temperature of less than 42° C.

23. The method according to claim 1 wherein said incubation in step (b) is halted by non-interfering means prior to performing step (c).

24. The method according to claim 23 wherein said non-interfering means comprises applying heat to the incubation media.

25. The method according to claim 23 wherein said non-interfering means comprises diluting the incubation media.

26. The method according to claim 23 wherein said non-interfering means comprises adding a deproteinizing agent to the incubation media.

27. The method according to claim 23 wherein said non-interfering means comprises adding a stopping buffer to the incubation media.

28. The method according to claim 27 wherein said stopping buffer has a pH value between 7 and 12.

29. The method according to claim 28, wherein said stopping buffer has a pH value between 10 and 11.

30. The method according to claim 1 comprising measuring said enzyme product with a fluorometer, a calorimeter, a spectrophotometer, or a radioactive counter.

31. The method according to claim 1, which comprises determining the amount of said enzyme product(s) present in said incubation media.

32. The method according to claim 1 wherein said dried blood spot is assayed within 40 days from collection.

33. The method according to claim 32 wherein said dried blood spot is assayed within 20 days from collection.

34. The method according to claim 33 wherein said dried blood spot is assayed within 24 hours from collection.

* * * * *